US009995728B2

(12) United States Patent
Fordham et al.

(10) Patent No.: US 9,995,728 B2
(45) Date of Patent: Jun. 12, 2018

(54) QUADRUPLEX METHOD

(71) Applicant: OXFORD NANOPORE TECHNOLOGIES LIMITED, Oxford (GB)

(72) Inventors: Daniel George Fordham, Oxford (GB); Nicholas Smith, Oxford (GB); Daniel John Turner, Oxford (GB)

(73) Assignee: Oxford Nanopore Technologies Ltd., Oxford (GB)

( * ) Notice: Subject to any disclaimer, the term of this patent is extended or adjusted under 35 U.S.C. 154(b) by 459 days.

(21) Appl. No.: 14/440,522

(22) PCT Filed: Nov. 6, 2013

(86) PCT No.: PCT/GB2013/052902
§ 371 (c)(1),
(2) Date: May 4, 2015

(87) PCT Pub. No.: WO2014/072703
PCT Pub. Date: May 15, 2014

(65) Prior Publication Data
US 2015/0301015 A1    Oct. 22, 2015

Related U.S. Application Data

(60) Provisional application No. 61/722,999, filed on Nov. 6, 2012.

(51) Int. Cl.
*C40B 30/04* (2006.01)
*G01N 33/487* (2006.01)
*C12Q 1/68* (2018.01)

(52) U.S. Cl.
CPC ..... *G01N 33/48721* (2013.01); *C12Q 1/6816* (2013.01); *C40B 30/04* (2013.01)

(58) Field of Classification Search
None
See application file for complete search history.

(56) References Cited

U.S. PATENT DOCUMENTS

| 5,576,204 | A | 11/1996 | Blanco et al. |
| 6,426,231 | B1 | 7/2002 | Bayley et al. |
| 8,105,846 | B2 | 1/2012 | Bayley et al. |
| 8,828,208 | B2 | 9/2014 | Canas et al. |

(Continued)

FOREIGN PATENT DOCUMENTS

| JP | 2010-524436 A | 7/2010 |
| WO | 00/28312 A1 | 5/2000 |

(Continued)

OTHER PUBLICATIONS

Altschul, S. F. (1993) J Mol Evol., 36: 290-300.
(Continued)

*Primary Examiner* — Christian C Boesen
(74) *Attorney, Agent, or Firm* — Wolf, Greenfield & Sacks, P.C.

(57) ABSTRACT

The invention relates to a new method of determining in a sample the presence, absence or concentration of one or more target analytes, such as micro-ribonucleic acids (microRNAs or miRNAs). The invention may therefore relate to a multiplex assay for determining the presence or absence of each target analyte in a group of multiple analytess. The invention uses one or more probes comprising a quadruplex and transmembrane pores.

16 Claims, 5 Drawing Sheets

(56) References Cited

U.S. PATENT DOCUMENTS

| | | |
|---|---|---|
| 2002/0197618 A1 | 12/2002 | Sampson |
| 2005/0014162 A1 | 1/2005 | Barth et al. |
| 2010/0196203 A1 | 8/2010 | Sanghera et al. |
| 2011/0120871 A1 | 5/2011 | Reid et al. |
| 2011/0121840 A1 | 5/2011 | Sanghera et al. |
| 2011/0177498 A1 | 7/2011 | Clarke et al. |
| 2011/0229877 A1 | 9/2011 | Jayasinghe et al. |
| 2012/0058468 A1 | 3/2012 | Mckeown |
| 2012/0100530 A1 | 4/2012 | Moysey et al. |
| 2012/0107802 A1 | 5/2012 | Stoddart et al. |
| 2012/0322679 A1 | 12/2012 | Brown et al. |
| 2014/0051069 A1 | 2/2014 | Jayasinghe et al. |
| 2014/0186823 A1 | 7/2014 | Clarke et al. |
| 2014/0296083 A1 | 10/2014 | Brown et al. |
| 2015/0008126 A1 | 1/2015 | Maglia et al. |
| 2015/0031020 A1 | 1/2015 | Jayasinghe et al. |
| 2015/0152492 A1 | 6/2015 | Brown et al. |
| 2015/0177237 A1 | 6/2015 | Turner et al. |
| 2015/0247183 A1 | 9/2015 | Turner et al. |
| 2015/0301015 A1 | 10/2015 | Fordham et al. |
| 2016/0010147 A1 | 1/2016 | Heron et al. |
| 2016/0251710 A1 | 9/2016 | Brown et al. |
| 2016/0257942 A1 | 9/2016 | Bruce et al. |

FOREIGN PATENT DOCUMENTS

| | | |
|---|---|---|
| WO | WO 2005/124888 | 12/2005 |
| WO | 2006/100484 A2 | 9/2006 |
| WO | 2008102120 A1 | 8/2008 |
| WO | 2008102121 A1 | 8/2008 |
| WO | WO 2008/124107 | 10/2008 |
| WO | 2009/035647 A1 | 3/2009 |
| WO | 2009/077734 A2 | 6/2009 |
| WO | WO 2009/046149 | 6/2009 |
| WO | 2010/004265 A1 | 1/2010 |
| WO | 2010/004273 A1 | 1/2010 |
| WO | 2010/086603 A1 | 8/2010 |
| WO | WO 2010/109197 | 9/2010 |
| WO | 2010/122293 A1 | 10/2010 |
| WO | 2011/067559 A1 | 6/2011 |
| WO | 2011103424 A2 | 8/2011 |
| WO | WO 2012/009578 | 1/2012 |
| WO | WO 2012/033524 | 3/2012 |
| WO | WO 2012/088339 A2 | 6/2012 |
| WO | WO 2012/129242 A2 | 9/2012 |
| WO | 2012/164270 A1 | 12/2012 |
| WO | WO 2013/014451 A1 | 1/2013 |
| WO | WO 2013/057495 A2 | 4/2013 |
| WO | WO 2013/098561 A1 | 7/2013 |
| WO | WO 2013/098562 A2 | 7/2013 |
| WO | WO 2013/121201 | 8/2013 |
| WO | 2013153359 A1 | 10/2013 |
| WO | WO 2014/013259 A1 | 1/2014 |
| WO | WO 2014/013260 A1 | 1/2014 |
| WO | WO 2014/013262 A1 | 1/2014 |
| WO | WO 2014/041337 A1 | 3/2014 |
| WO | 2014072703 A1 | 5/2014 |
| WO | WO 2014/135838 A1 | 9/2014 |
| WO | WO 2015/055981 A2 | 4/2015 |
| WO | WO 2015/056028 A1 | 4/2015 |
| WO | WO 2015/110777 A1 | 7/2015 |
| WO | WO 2015/150786 A1 | 10/2015 |

OTHER PUBLICATIONS

Altschul, S.F et al.,(1990) J Mol Biol., 215: 403-410.
Anderson, N.L. et al., (2010) Clin. Chem., 56: 177-185.
Barshack et al., (2010) The International Journal of Biochemistry & Cell Biology 42: 1355-1362.
Berezovski, M. et al., (2006) Journal of the American Chemical Society, 128: 1410-1411.
Bock, L. C. et al., (1992) Nature, 355: 564-566.
Chen et al., (2005) Nucleic Acids Research, 33 (20): e179.
Chen et al., (2008) Nucleic Acids Research, 36 (14): e87.
Cissell et al., (2008) Analytical Chemistry 80: 2319-2325.
Devereux et al., (1984) Nucleic Acids Research, 12: 387-395.
Edwards, A.V.G. et al., (2008) Mol. Cell. Proteomics, 7: 1824-1837.
Esquela-Kerscher et al, (2006) Cancer, 6: 259-269.
Gilad et al., (2008) PloS One, vol. 3, Issue 9, e3148.
Gonzalez-Perez et al, (2009) Langmuir, 25: 10447-10450.
Grant and Qin, (2007) Nucleic Acids Res., 35(10): e77.
Gu et al., (2010) The Analyst,135 (5): 441-451.
Gu, et al, (Jul. 2012) Expert Rev Mol Diagn., 12(6): 573-584.
Hall et al., (2010) Nat Nanotechnol., 5(12): 874-877.
Holden et al., (2007) J Am Chem Soc., 29(27):8650-8655.
Holden, et al., (2005) J. Am. Chem. Soc., 127, 6502-6503.
Hornblower et al, (2007) Nature Methods, 4: 315-317.
Jacquet, S. et al, (2009), Mol. Cell. Proteomics, 8: 2687-2699.
Jiang Q. et al., (2009) Nucleic Acids Res, 37: D98-D104.
Kankia and Marky, (2001) J. Am. Chem. Soc., 123: 10799-10804.
Keller et al., (2011) Nature Methods 8, 841-843.
Khan et al, (2011) Analytical Chemistry, 83: 6196-6201.
Kirschner et al., (2011) PloS One, 6: e24145.
Kozarewa, I. et al, (2011), Methods Mol. Biol., 733: 279-298.
Krichevsky et al., (2003) RNA, 9: 1274-1281.
Kumar, et al. (1988) Anal Biochem, 169(2): 376-382.
Lee et al., (1993) Cell 75: 843-854.
Lewis et al, (2005) Cell 120: 15-20.
Lieberman, K.R. et al, (2010) J Am Chem Soc., 132(50):17961-17972.
Lu et al., (2005) Nature, 834-838.
Marathias and Bolton, (2000) Nucleic Acids Research, 28(9): 1969-1977.
Marusic et al., (2012) Nucleic Acids Research, 1-11.
Montal and Mueller, (1972) Proc. Natl. Acad. Sci. USA., 69(12): 3561-3566.
Movileanu et al, (Jun. 2009), Trends in Biotechnology, 27(6):333-341.
Murphy et al, Expert Review of Molecular Diagnostics 9, 187-97 (2009).
Nasheri et al., (2011) Analytical Biochemistry, 412:165-172.
Nikolov, et al., (2007) Biophys J, 92(12): 4356-4368.
Pfeiffer and Hook, (2004) J Am Chem Soc., 126(33): 10224-10225.
Reinhart et al., (2002) Genes & Development 16(13): 1616-1626.
Rosenfeld, N. et al., (2008) Nature Biotechnology, 26: 462-469.
Rotem, D. et al, (2012) JACS, 134 (5) 2781-2787.
Shim, J.W. et al, (Dec. 2008) Nucleic Acids Research, 37(3): 972-982.
Stoddart, D. S., et al, (2009), Proceedings of the National Academy of Sciences of the United States of America, 106: 7702-7707.
Stoltenburg, R. et al, (2007) Biomolecular Engineering, 24: 381-403.
Troutt et al., (1992) Proc Natl Acad Sci USA, 89(20): 9823-9825.
Tuerk, C. et al., (1990) Science, 249: 505-510.
Actis et al., Reversible thrombin detection by aptamer functionalized STING sensors. Biosens Bioelectron. Jul. 15, 2011;26(11):4503-7. doi: 10.1016/j.bios.2011.05.010. Epub May 12, 2011.
Ayub et al., Individual RNA base recognition in immobilized oligonucleotides using a protein nanopore. Nano Lett. Nov. 14, 2012;12(11):5637-43. doi: 10.1021/nl3027873. Epub Oct. 19, 2012.
Braha et al., Designed protein pores as components for biosensors. Chem Biol. Jul. 1997;4(7):497-505.
Branton et al., The potential and challenges of nanopore sequencing. Nat Biotechnol. Oct. 2008;26(10):1146-53. doi:10.1038/nbt.1495.
Chandler et al., Membrane surface dynamics of DNA-threaded nanopores revealed by simultaneous single-molecule optical and ensemble electrical recording. Langmuir. Feb. 3, 2004;20(3):898-905.
Cheng et al., DNA strand transfer catalyzed by vaccinia topoisomerase:ligation of DNAs containing a 3' mononucleotide overhang. Nucleic Acids Res. May 1, 2000;28(9):1893-8.

(56) References Cited

OTHER PUBLICATIONS

Cockroft et al., A single-molecule nanopore device detects DNA polymerase activity with single-nucleotide resolution. J Am Chem Soc. Jan. 23, 2008;130(3):818-20. doi: 10.1021/ja077082c. Epub Jan. 1, 2008.

Dahl et al., Direct observation of translocation in individual DNA polymerase complexes. J Biol Chem. Apr. 13, 2012;287(16):13407-21. doi:10.1074/jbc.M111.338418. Epub Feb. 29, 2012.

Deamer, Nanopore analysis of nucleic acids bound to exonucleases and polymerases. Annu Rev Biophys. 2010;39:79-90. doi:10.1146/annurev.biophys.093008.131250.

Dong et al., Wza the translocon for *E. coli* capsular polysaccharides defines a new class of membrane protein. Nature. Nov. 9, 2006;444(7116):226-9.

Eliseev et al., Molecular Recognition of Nucleotides, Nucleosides, and Sugars by Aminocyclodextrins. J. Am. Chem. Soc., vol. 116:6081-6088 (1994).

Ivanov et al., DNA tunneling detector embedded in a nanopore. Nano Lett. Jan. 12, 2011;11(1):279-85. doi: 10.1021/nl103873a. Epub Dec. 6, 2010.

Kocalka et al., Rapid and efficient DNA strand cross-linking by click chemistry. Chembiochem. May 23, 2008;9(8):1280-5. doi:10.1002/cbic.200800006.

Kolb et al., Click Chemistry: Diverse Chemical Function from a Few Good Reactions. Angew Chem Int Ed Engl. Jun. 1, 2001;40(11):2004-2021.

Langecker et al., Synthetic lipid membrane channels formed by designed DNA nanostructures. Science. Nov. 16, 2012;338(6109):932-6. doi: 10.1126/science.1225624.

Loakes, Survey and summary: The applications of universal DNA base analogues. Nucleic Acids Res. Jun. 15, 2001;29(12):2437-47.

Manrao et al., Reading DNA at single-nucleotide resolution with a mutant MspA nanopore and phi29 DNA polymerase. Nat Biotechnol. Mar. 25, 2012;30(4):349-53. doi: 10.1038/nbt.2171.

Sekiguchi et al., Kinetic analysis of DNA and RNA strand transfer reactions catalyzed by vaccinia topoisomerase. J Biol Chem. Jun. 20, 1997;272(25):15721-8.

Shi et al., 5' RACE by tailing a general template-switching oligonucleotide. Biotechniques. Dec. 2000;29(6):1192-5. Erratum in: Biotechniques May 2001;30(5):934.

Stoddart et al., Single-nucleotide discrimination in immobilized DNA oligonucleotides with a biological nanopore. Proc Natl Acad Sci U S A. May 12, 2009;106(19):7702-7. doi: 10.1073/pnas.0901054106. Epub Apr. 20, 2009.

Tazi et al., Alternative splicing and disease. Biochim Biophys Acta. Jan. 2009;1792(1):14-26. doi: 10.1016/j.bbadis.2008.09.017. Epub Oct. 17, 2008.

Tian et al., Designing a polycationic probe for simultaneous enrichment and detection of microRNAs in a nanopore. ACS Nano. May 28, 2013;7(5):3962-9. doi: 10.1021/nn305789z. Epub Apr. 10, 2013.

Wang et al., Nanopore-based detection of circulating microRNAs in lung cancer patients. Nat Nanotechnol. Sep. 4, 2011;6(10):668-74. doi: 10.1038/nnano.2011.147.

Wanunu et al., Rapid electronic detection of probe-specific microRNAs using thin nanopore sensors. Nat Nanotechnol. Nov. 2010;5(11):807-14. doi: 10.1038/nnano.2010.202. Epub Oct. 24, 2010.

White et al., Generation of species cross-reactive aptamers using "toggle" SELEX. Mol Ther. Dec. 2001;4(6):567-73.

Van Heel M, et al., (2000) Q Rev Biophys., 33 (4): 307-369.

Van Lengerich, et al., (2010) Langmuir, 26(11): 8666-8672.

Venkatesan et al, (2011) Nature Nanotechnology, 6 (10): 615-624.

Wang et al., (2010) Biochemical and Biophysical Research Communications, 394: 184-188.

Wightman et al., (1993) Cell, 75: 855-862.

Yoshina-Ishii, C. et al., (2003) J Am Chem Soc., 125(13): 3696-3697.

International Search Report and Written Opinion, PCT/GB2013/052902, dated Jan. 3, 2014, pp. 1-12.

International Preliminary Report on Patentability, PCT/GB2013/052902, dated May 12, 2015, pp. 1-7.

U.S. Appl. No. 14/378,929, filed Aug. 14, 2014, Daniel John Turner.

U.S. Appl. No. 13/260,178, filed Jan. 17, 2012, David Stoddart.

U.S. Appl. No. 14/334,285, filed Jul. 17, 2014, Giovanni Maglia.

U.S. Appl. No. 13/984,628, filed Feb. 27, 2014, James Clarke.

U.S. Appl. No. 13/002,717, filed Mar. 30, 2011, James Clarke.

U.S. Appl. No. 14/455,394, filed Aug. 8, 2014, Lakmal Jayasinghe.

U.S. Appl. No. 13/968,778, filed Aug. 16, 2013, Lakmal Jayasinghe.

U.S. Appl. No. 12/093,610, filed Jul. 28, 2008, Hagan Bayley.

QUADRUPLEX METHOD

CROSS REFERENCE TO RELATED APPLICATIONS

This application is a 35 U.S.C. 371 national stage filing of International Application No. PCT/GB2013/052902, filed on Nov. 6, 2013, which claims priority to U.S. Provisional Patent Application No. 61/722,999, filed on Nov. 6, 2012. The contents of the aforementioned applications are hereby incorporated by reference in their entireties.

FIELD OF THE INVENTION

The invention relates to a new method of determining in a sample the presence, absence or concentration of one or more target analytes, such as micro-ribonucleic acids (microRNAs or miRNAs). The invention may therefore relate to a multiplex assay for determining the presence or absence of each target analyte in a group of multiple analytes. The invention uses one or more probes comprising a quadruplex and transmembrane pores.

BACKGROUND OF THE INVENTION

There is a need for techniques which can detect the presence of low concentrations of analytes with high accuracy, particularly when multiple analytes are present in a single sample. The need is particularly acute for detection of biomarkers and thus the diagnosis of the associated disease or disorder. One group of biomarkers which are difficult to detect in low concentrations are micro-ribonucleic acids (micro-RNA or miRNAs). miRNAs are highly stable RNA oligomers, which can regulate protein production post-transcriptionally. They act by one of two mechanisms. In plants, miRNAs have been shown to act chiefly by directing the cleavage of messenger RNA, whereas in animals, gene regulation by miRNAs typically involves hybridisdation of miRNAs to the 3' UTRs of messenger RNAs, which hinders translation (Lee et al., Cell 75, 843-54 (1993); Wightman et al., Cell 75, 855-62 (1993); and Esquela-Kerscher et al., Cancer 6, 259-69 (2006)). miRNAs frequently bind to their targets with imperfect complementarity. They have been predicted to bind to as many as 200 gene targets each and to regulate more than a third of all human genes (Lewis et al., Cell 120, 15-20 (2005)).

The expression level of certain microRNAs is known to change in tumours, giving different tumour types characteristic patterns of microRNA expression (Rosenfeld, N. et al., Nature Biotechnology 26, 462-9 (2008)). In addition, miRNA profiles have been shown to be able to reveal the stage of tumour development with greater accuracy than messenger RNA profiles (Lu et al., Nature 435, 834-8 (2005) and Barshack et al., The International Journal of Biochemistry & Cell Biology 42, 1355-62 (2010)). These findings, together with the high stability of miRNAs, and the ability to detect circulating miRNAs in serum and plasma (Wang et al., Biochemical and Biophysical Research Communications 394, 184-8 (2010); Gilad et al., PloS One 3, e3148 (2008); and Keller et al., Nature Methods 8, 841-3 (2011)), have led to a considerable amount of interest in the potential use of microRNAs as cancer biomarkers. For treatment to be effective, cancers need to be classified accurately and treated differently, but the efficacy of tumour morphology evaluation as a means of classification is compromised by the fact that many different types of cancer share morphological features. miRNAs offer a potentially more reliable and less invasive solution.

The physiological concentration of microRNAs varies over a wide range, such as from low nM to fmol, and probably lower (Kirschner et al., PloS One 6, e24145 (2011) and the difference in expression level between different stages of cancers can be slight (Barshack et al., supra) so quantification with high sensitivity and accuracy is essential if a diagnostic test is to be useful.

Several methods have been used to identify and quantify miRNAs, such as Northern blotting (Reinhart et al., Genes & Development 16, 1616-26 (2002)), hybridisation to arrays (Chen et al., Nucleic Acids Research 36, e87 (2008) and Krichevsky et al., RNA 9, 1274-81 (2003)) and reverse transcription polymerase chain reaction, RT-PCR (Chen et al., Nucleic Acids Research 33, e179 (2005)). However, each approach has several shortcomings. For instance, Northern blots use a large quantity of total RNA, are not high throughput, are not readily multiplexed and are not strictly quantitative. Arrays have the advantage of being able to quantify many miRNAs at once but, as with Northern blots, lack sensitivity, need large amounts of RNA, or amplification, are not quantitative and also suffer from probe cross-hybridisation. Reverse transcriptase qPCR is considered to be inaccurate, is prone to primer cross-hybridisation if done in multiplex and results are often inconsistent between different laboratories (Murphy et al., Expert Review of Molecular Diagnostics 9, 187-97 (2009)). Furthermore, all of these methods require the use of RNA extraction kits to isolate and concentrate total RNA, which is inconvenient.

The ideal method for miRNA quantification would by highly sensitive, would not require a large amount of starting material, would be high throughput, capable of multiplexed measurement, would not require amplification of the RNA and could be performed directly on blood, serum or plasma. A small number of methods have been described which are capable of detecting and quantifying miRNA directly from cell lysate including surface Plasmon resonance and protein facilitated affinity capillary electrophoresis (Cissell et al., Analytical Chemistry 80, 2319-25 (2008); Nasheri et al., Analytical Biochemistry 412, 165-72 (2011); and Khan et al., Analytical Chemistry 83, 6196-201 (2011)), but these approaches require expensive hardware and have not been demonstrated to have multiplexing capability.

Transmembrane pores (nanopores) have great potential as direct, electrical biosensors for a variety of analytes, such as polymers and small molecules. When a potential is applied across a nanopore, there is a change in the current flow when a molecule, such as a nucleotide or a polynucleotide, resides transiently in the barrel or channel of the nanopore for a certain period of time. Specific molecules, such as specific nucleotides and specific polynucleotides, give current changes of known signature and duration. Such current changes can be used to identify the nucleotide or polynucleotide present in the pore.

SUMMARY OF THE INVENTION

The inventors have demonstrated that quadruplexes can be used in a nanopore-based assay to determine the presence, absence or concentration of an analyte. The assay is ideal for determining the presence, absence or concentration of one or more analytes. The assay may detect one target analyte, such as one miRNA, or may be a multiplex assay that is capable of detecting more than one target analyte, such as more than one miRNA.

More specifically, the inventors have demonstrated that the presence, absence or concentration of a target analyte can be determined in a uniplex assay using a transmembrane pore and a probe comprising a quadruplex-containing detection unit. The unit comprises three parts. The first is a section which is capable of translocating through the pore and which specifically binds to the target analyte and thereby specifically recognises the target analyte. The second is a sequence which is capable of forming a quadruplex. The quadruplex is not capable of translocating through the narrowest part of the pore. The third is a region which is capable of entering the narrowest part of the pore when the quadruplex cannot and which affects the current flowing through the pore in a distinctive manner. As discussed in more detail below, both the complex formed by binding of the first part of the unit to the target analyte and the quadruplex temporarily prevent the probe from passing through the pore. Both braking events result in measurable changes in the current flowing through the pore. By measuring the current flowing through the pore, it is possible to detect binding of the first part of the unit to the target analyte and thereby determine the presence, absence or concentration of the target analyte. The identity of the probe may be confirmed using the distinctive current produced by the region as it is temporarily held in the pore by the braking action of the quadruplex.

The inventors have also demonstrated that the presence, absence or concentration of more than one target analyte (i.e. two or more target analytes) can be determined in a multiplex assay using a transmembrane pore and multiple repetitions of the detection unit defined above. Each repeating unit specifically recognises one of the target analytes. The repeating units may either be in one probe or in multiple probes. As above, the presence of a target analyte may be detected by the change in current associated with the braking action of a complex formed by binding of the first part of the unit to the target analyte. The identity of each repeating unit and by association the identity of each target analyte may be determined using the distinctive current generated by the third part of each unit as it is temporarily held in the narrowest part of the pore by the braking action of the quadruplex.

Accordingly, the invention provides a method of determining in a sample the presence or absence of a target analyte, the method comprising:

(a) contacting the target analyte with a transmembrane pore and a probe, wherein the probe comprises (i) a section which is capable of translocating through the pore and which specifically binds to the target analyte, (ii) at least one sequence which is capable of forming a quadruplex, wherein the quadruplex is not capable of translocating through the narrowest part of the pore, and (iii) at least one region which is capable of entering the narrowest part of the pore when the quadruplex formed by sequence (ii) cannot and which affects the current flowing through the pore in a distinctive manner; and (b) measuring the current flowing through the pore to determine whether or not the probe has bound to the target analyte and thereby determining the presence or absence of the target analyte in the sample.

The invention also provides a method of determining in a sample the presence or absence of one or more members of a group of two or more target analytes, the method comprising:

(a) contacting the sample with a transmembrane pore and one or more probes, wherein each probe comprises one or more repeating units, wherein each repeating unit specifically recognises one of the members, wherein each repeating unit comprises (i) a section which is capable of translocating through the pore and which specifically binds to the member, (ii) at least one sequence which is capable of forming a quadruplex, wherein the quadruplex is not capable of translocating through the narrowest part of the pore, and (iii) at least one region which is capable of entering the narrowest part of the pore when the quadruplex formed by sequence (ii) cannot and which affects the current flowing through the pore in a distinctive manner, and wherein each member of the group is specifically recognised by at least one repeating unit in the one or more probes; and (b) measuring the current flowing through the pore to determine which repeating units in the one or more probes, if any, have bound to a member and thereby determining the presence or absence of one or more members in the sample.

The invention also provides:

a method of determining in a sample the concentration of a target analyte, the method comprising:

(i) carrying out a uniplex method of the invention; and (ii) if the target analyte is shown to be present in the sample comparing the current flowing through the pore in step (b) with control or reference data for the target analyte and thereby determining the concentration of the target analyte in the sample;

a method of determining in a sample the concentration of one or more members of a group of two or more target analytes, the method comprising:

(i) carrying out a multiplex method of the invention; and (ii) for one or more members shown to be present in the sample comparing the current flowing through the pore in step (b) with control or reference data for each member and thereby determining the concentration of the one or more members in the sample;

a probe for determining the presence, absence or concentration of a target analyte, the probe comprising (i) a section which specifically binds to the target analyte, (ii) at least one sequence which is capable of forming a quadruplex, and (iii) at least one region which is specific for the section (i);

a probe for determining the presence, absence or concentration of one or more members of a group of two or more target analytes, the probe comprising two or more repeating units, wherein each repeating unit comprises (i) a section which specifically binds to one of the members, (ii) at least one sequence which is capable of forming a quadruplex, and (iii) at least one region which is specific for the section (i), and wherein each member is specifically recognised by at least one repeating unit;

a panel of probes for determining in a sample the presence, absence or concentration of one or more members of a group of two or more target analytes, the panel comprising two or more probes, wherein each probe comprises one or more repeating units, wherein each repeating unit specifically recognises one of the members, wherein each repeating unit comprises (i) a section which specifically binds to the member, (ii) at least one sequence which is capable of forming a quadruplex, and (iii) at least one region which is specific for the section (i), and wherein each member of the group is specifically recognised by at least one repeating unit in the two or more probes;

a kit for determining in a sample the presence, absence or concentration of a target analyte or one or more members of a group of two or more target analytes, comprising (a) a probe of the invention or a panel of probes of the invention and (b) a transmembrane pore; and an analysis apparatus for determining in a sample the presence, absence or concentration of a target analyte or one or more members of a group of two or more target analytes, comprising (a) a plurality of transmembrane pores and (b) a plurality of probes according of the invention, a multiplex probe of the invention or a panel of probes of the invention.

DESCRIPTION OF THE SEQUENCE LISTING

Figure 1:
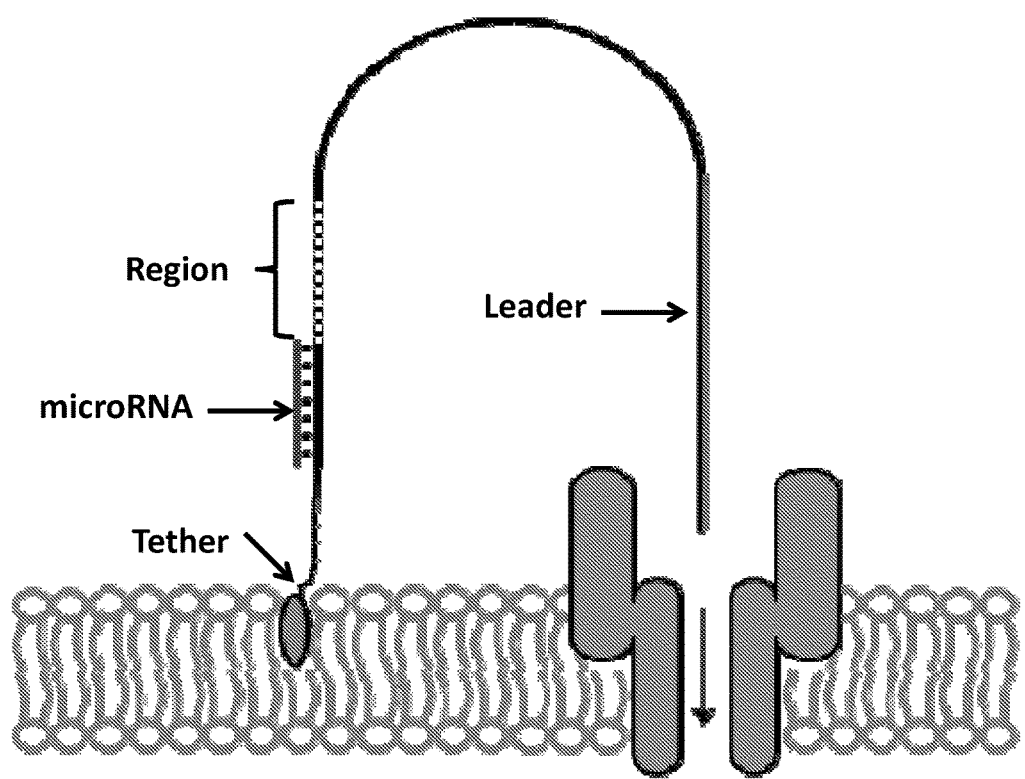
FIG. 1 shows the comparative probe design used in Example 1.

SEQ ID NO: 1 shows the polynucleotide sequence encoding one subunit of α-hemolysin-E111N/K147N (α-HL-NN; (Stoddart, D. S., et al., (2009), *Proceedings of the National Academy of Sciences of the United States of America* 106, p 7702-'7'70'7).

SEQ ID NO: 2 shows the amino acid sequence of one subunit of α-HL-NN.

SEQ ID NO: 3 shows the polynucleotide sequence enocoding the LukF subunit of γ-hemolysin.

SEQ ID NO: 4 shows the amino acid sequence of the LukF subunit of γ-hemolysin.

SEQ ID NO: 5 shows the polynucleotide sequence enocoding the Hlg2 subunit of γ-hemolysin.

SEQ ID NO: 6 shows the amino acid sequence of the Hlg2 subunit of γ-hemolysin.

SEQ ID NOs: 7 to 11 show the sequences used in the Examples. SEQ ID NOs: 9 and 10 are not included in the actual sequence listing because they do not comply with WIPO's Standard ST.25. They contain abasic nucleotides which are not present in Table 2 of the Standard. The sequences of SEQ ID NOs: 9 and 10 are shown in the Examples.

DETAILED DESCRIPTION OF THE INVENTION

It is to be understood that different applications of the disclosed products and methods may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural referents unless the content clearly dictates otherwise. Thus, for example, reference to "a pore" includes two or more such pores, reference to "a sequence" includes two or more such sequences, reference to "a region" includes two or more such regions, reference to "a polynucleotide" includes two or more such polynucleotides, and the like.

All publications, patents and patent applications cited herein, whether supra or infra, are hereby incorporated by reference in their entirety.

Methods of the Invention

The invention provides a method of determining in a sample the presence or absence of a target analyte. The method therefore concerns measuring one target analyte. This method is a uniplex method. The target analyte is predetermined. The method uses a probe that is designed to specifically recognise the target analyte. The probe comprises a section (i) which specifically binds to the target analyte. This is discussed in more detail below.

The uniplex method comprises contacting the sample with a transmembrane pore and a probe comprising a detection unit. The unit comprises a section that is capable of translocating through the pore and which specifically binds to and therefore specifically detects the target analyte. This is labelled (i) above and below. The complex formed by binding of this section to the target analyte temporarily prevents the probe from translocating or moving through the pore. This braking action temporarily holds part of the probe, preferably a spacer (iv), in the narrowest part of the pore and this results in a change in the current flowing through the pore. Typically, it temporarily results in a steady current flowing through the pore. The change in current may be measured and used to confirm that the probe has bound to its target analyte and thereby confirm the presence of the target analyte.

The unit also comprises at least one sequence which is capable of forming a quadruplex. This is labelled (ii) above and below. The quadruplex cannot translocate or move through the narrowest part of the pore and so temporarily prevents the probe from translocating or moving through the pore.

The unit also comprises at least one region which is capable of entering the narrowest part of the pore when the quadruplex cannot and which affects the current flowing through the pore in a distinctive manner. This is labelled (iii) above and below. The distinctive current flowing through the pore when the quadruplex temporarily prevents movement of the probe through the pore can be used to identify the unit and probe. For instance, control experiments may be carried out to confirm the effect of the region on the current flowing through pore and subsequent measurement of the same or similar current may be used to identify the region and by association the unit and probe.

The uniplex method also comprises measuring the current flowing through the pore to determine whether or not the probe has bound to the target analyte and thereby determining the presence or absence of the target analyte in the sample. The current may be measured using any method known in the art. Specific methods are discussed below. If the probe binds to the target analyte to which its section (i) specifically binds, the target analyte is present in the sample. If the probe does not bind to the target analyte to which its section (i) specifically binds, the target analyte is not present in the sample (i.e. is absent from the sample).

The invention also provides a method of determining in a sample the presence or absence of one or more members of a group of two or more target analytes. This is a multiplex method. The two or more target analyte s in the group are predetermined. The multiplex method therefore concerns determining the presence or absence of each member of a specific and predetermined group of two or more target analytes. In the multiplex method, multiple repeating units as defined above are used. In order for the multiplex method to work effectively, each member of the group must be specifically recognised by at least one repeating unit.

The multiplex method comprises contacting the sample with a transmembrane pore and one or more probes each of which comprise one or more repeating units as defined above. The one or more probes are a probe or a panel of two or more probes. Each repeating unit specifically recognises one of the members of the group of two or more target analytes.

In the multiplex method, the presence of a target analyte is detected by measuring the change in current associated with the braking action of the complex resulting from the specific binding of the section (i) to the target analyte. The complex temporarily holds a part of the probe, preferably a spacer (iv), in the narrowest part of the pore and this results in a change in current flowing through the pore. Typically, it temporarily results in a steady current flowing through the pore. The identity of the repeating unit is determined by the distinctive current provided by the region (iii) when the quadruplex formed by sequence (ii) temporarily prevents the unit from translocating or moving through the pore. Since both the binding of each repeating unit to its target analyte and the identity of each repeating unit can be measured, the presence of each target analyte can be determined.

The multiplex method also comprises measuring the current flowing through the pore to determine which repeating units in the one or more probes, if any, have bound to a target analyte and thereby determining the presence or absence of one or more target analytes in the sample. The current may be measured using any method known in the art. Specific methods are discussed below. If a repeating unit binds to the target analyte to which it specifically binds, the target analyte is present in the sample. If a repeating unit does not bind to the target analyte to which it specifically binds, the target analyte is not present in the sample (i.e. is absent from the sample).

Steps (a) and (b) in the uniplex and multiplex methods are preferably carried out with a potential applied across the pore. The applied potential typically causes the probe to translocate or move through the pore. As discussed above, the movement or translocation of the probe through the pore may be temporarily interrupted by the quadruplex formed from sequence (ii) and, if the target analyte is present, the complex formed by the binding of section (i) to the target analyte. The former interruption identifies the probe or repeating unit (and hence by association the target analyte) and the latter interruption indicates that the target analyte is present. The applied potential may be a voltage potential. Alternatively, the applied potential may be a chemical potential. An example of this is using a salt gradient across an amphiphilic layer. A salt gradient is disclosed in Holden et al., J Am Chem Soc. 2007 Jul. 11; 129(27):8650-5.

The methods of the invention have several advantages. The uniplex method is highly sensitive, does not require a large amount of starting material, has a high throughput, does not require amplification of target polynucleotides and can be performed directly on blood, serum or plasma. The multiplex method has the same advantages and is capable of detecting multiple target analytes at a time. The multiplex method can be used to detect many target analytes from a single sample, thus obviating the need for multiple tests on a single sample, the number of target analytes being limited only by the diversity and number of distinct repeating units which can be generated.

Both methods are rapid and cheap compared to existing assays, whilst still having high specificity. Probes containing polynucleotide sequences are quick and cheap to prepare in comparison to, for example, antibodies. The output from both methods is analysed in real time, allowing them to be stopped when sufficient information has been obtained. The methods can be carried out by someone with minimal training or qualification.

Sample

The sample may be any suitable sample. The invention is typically carried out on a sample that is known to contain or suspected of containing one or more target analytes. The invention may be carried out on a sample that contains one or more target analytes whose identity is unknown. Alternatively, the invention may be carried out on a sample to confirm the identity of one or more target analytes whose presence in the sample is known or expected.

The sample may be a biological sample. The invention may be carried out in vitro on a sample obtained from or extracted from any organism or microorganism. The organism or microorganism is typically archaean, prokaryotic or eukaryotic and typically belongs to one the five kingdoms: plantae, animalia, fungi, monera and protista. The invention may be carried out in vitro on a sample obtained from or extracted from any virus. The sample is preferably a fluid sample. The sample typically comprises a body fluid of the patient. The sample may be urine, lymph, saliva, mucus, milk or amniotic fluid but is preferably blood, plasma or serum. Typically, the sample is human in origin, but alternatively it may be from another mammal animal such as from commercially farmed animals such as horses, cattle, sheep or pigs or may alternatively be pets such as cats or dogs. Alternatively a sample of plant origin is typically obtained from a commercial crop, such as a cereal, legume, fruit or vegetable, for example wheat, barley, oats, canola, maize, soya, rice, bananas, apples, tomatoes, potatoes, grapes, tobacco, beans, lentils, sugar cane, cocoa, cotton, tea, coffee.

The sample may be a non-biological sample. The non-biological sample is preferably a fluid sample. Examples of a non-biological sample include surgical fluids, water such as drinking water, sea water or river water, and reagents for laboratory tests.

The sample is typically processed prior to being assayed, for example by centrifugation or by passage through a membrane that filters out unwanted molecules or cells, such as red blood cells. The sample may be measured immediately upon being taken. The sample may also be typically stored prior to assay, preferably below −70° C.

Analyte

The method of the invention is for determining in a sample the presence or absence of one (uniplex method) or more than one (multiplex method) target analyte. In the uniplex method, the target analyte is either present or absent.

In the multiplex method, the presence or absence of one or more members of a group of two or more target analytes is determined. The group of two or more target analytes may comprise any number of analytes such as 2, 5, 10, 15, 20, 30, 40, 50, 100, 500, 1000, 1500, 1750, 2000 or more analytes. The group preferably has from about 2 to about 2000 analytes, such as from about 5 to about 1500 analytes, from about 10 to about 1000 analytes, from about 20 to about 500 analytes or from about 50 to about 100 analytes. 1754 human miRNAs have been identified to date.

In the multiplex method, the presence or absence of one or more of the analyte members is determined. In other words, for a group of two or more analytes, the method determines whether each of the analyte members in the group is present or absent. One or more, such as 2, 5, 10, 15, 20, 30, 40, 50, 100 or more, of the analyte members may be present and all of the other analyte members in the group may be absent. All of the analyte members may be present. None of the analyte members may be present (i.e. all of the analyte members may be absent). The number of analyte members that are present and the number that are absent are determined using the multiplex method of the invention.

The analyte is preferably selected from metal ions, inorganic salts, polymers, amino acids, peptides, polypeptides, proteins, nucleotides, oligonucleotides, polynucleotides, dyes, bleaches, pharmaceuticals, diagnostic agents, recreational drugs, explosives and environmental pollutants. In the multiplex method, the group may comprise two or more analytes of the same type, such as two or more proteins, two or more nucleotides or two or more pharmaceuticals. Alternatively, the group may comprise two or more analytes of different types, such as one or more proteins, one or more nucleotides and one or more pharmaceuticals.

The analyte can be an analyte that is secreted from cells. Alternatively, the analyte can be an analyte that is present inside cells such that the analyte must be extracted from the cells before the invention can be carried out.

The analyte is preferably selected from amino acids, peptides, polypeptides and/or proteins. The amino acid, peptide, polypeptide or protein can be naturally-occurring or non-naturally-occurring. The polypeptide or protein can include within them synthetic or modified amino acids. A number of different types of modification to amino acids are known in the art. Suitable amino acids and modifications thereof are discussed below with reference to the transmembrane pore. For the purposes of the invention, it is to be understood that the analyte can be modified by any method available in the art.

The protein can be selected from enzymes, antibodies, hormones, growth factors or growth regulatory proteins, such as cytokines. The cytokine may be selected from interleukins, preferably IFN-1, IL-1, IL-2, IL-4, IL-5, IL-6, IL-10, IL-12 and IL-13, interferons, preferably IL-γ, and other cytokines such as TNF-α. The protein may be a bacterial protein, a fungal protein, a viral protein or a parasite-derived protein.

The analyte is preferably selected from nucleotides, oligonucleotides and/or polynucleotides. A nucleotide typically contains a nucleobase, a sugar and at least one phosphate group. The nucleobase is typically heterocyclic. Nucleobases include, but are not limited to, purines and pyrimidines and more specifically adenine (A), guanine (G), thymine (T), uracil (U) and cytosine (C). The sugar is typically a pentose sugar. Nucleotide sugars include, but are not limited to, ribose and deoxyribose. The nucleotide is typically a ribonucleotide or deoxyribonucleotide. The nucleotide typically contains a monophosphate, diphosphate or triphosphate. Phosphates may be attached on the 5' or 3' side of a nucleotide.

Nucleotides include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), 5-methylcytidine monophosphate, 5-methylcytidine diphosphate, 5-methylcytidine triphosphate, 5-hydroxymethylcytidine monophosphate, 5-hydroxymethylcytidine diphosphate, 5-hydroxymethylcytidine triphosphate, cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP), 5-methyl-2'-deoxycytidine monophosphate, 5-methyl-2'-deoxycytidine diphosphate, 5-methyl-2'-deoxycytidine triphosphate, 5-hydroxymethyl-2'-deoxycytidine monophosphate, 5-hydroxymethyl-2'-deoxycytidine diphosphate and 5-hydroxymethyl-2'-deoxycytidine triphosphate. The nucleotides are preferably selected from AMP, TMP, GMP, UMP, dAMP, dTMP, dGMP or dCMP. The nucleotides may be abasic (i.e. lack a nucleobase). The nucleotides may contain additional modifications. In particular, suitable modified nucleotides include, but are not limited to, 2'amino pyrimidines (such as 2'-amino cytidine and 2'-amino uridine), 2'-hyrdroxyl purines (such as, 2'-fluoro pyrimidines (such as 2'-fluorocytidine and 2'fluoro uridine), hydroxyl pyrimidines (such as 5'-α-P-borano uridine), 2'-O-methyl nucelotides (such as 2'-O-methyl adenosine, 2'-O-methyl guanosine, 2'-O-methyl cytidine and 2'-O-methyl uridine), 4'-thio pyrimidines (such as 4'-thio uridine and 4'-thio cytidine) and nucleotides have modifications of the nucleobase (such as 5-pentynyl-2'-deoxy uridine, 5-(3-aminopropyl)-uridine and 1,6-diaminohexyl-N-5-carbamoylmethyl uridine).

A nucleotide may be abasic (i.e. lack a nucleobase). A nucleotide may also lack a nucleobase and a sugar (i.e. is a C3 spacer).

Oligonucleotides are short nucleotide polymers which typically have 50 or fewer nucleotides, such 40 or fewer, 30 or fewer, 20 or fewer, 10 or fewer or 5 or fewer nucleotides. The oligonucleotides may comprise any of the nucleotides discussed above, including the abasic and modified nucleotides.

A polynucleotide, such as a nucleic acid, is a macromolecule comprising two or more nucleotides. The polynucleotide or nucleic acid may comprise any combination of any nucleotides. The nucleotides can be naturally occurring or artificial. One or more nucleotides in the target polynucleotide can be oxidized or methylated. One or more nucleotides in the template polynucleotide may be damaged. For instance, the polynucleotide may comprise a pyrimidine dimer. Such dimers are typically associated with damage by ultraviolet light and are the primary cause of skin melanomas. One or more nucleotides in the template polynucleotide may be modified, for instance with a label or a tag. Suitable labels are described below. The template polynucleotide may comprise one or more spacers.

The nucleotides in the polynucleotide may be attached to each other in any manner. The nucleotides are typically attached by their sugar and phosphate groups as in nucleic acids. The nucleotides may be connected via their nucleobases as in pyrimidine dimers.

The polynucleotide may be double stranded. The polynucleotide is preferably single stranded. The polynucleotide may be one strand from a double stranded polynucleotide.

The polynucleotides can be nucleic acids, such as deoxyribonucleic acid (DNA) or a ribonucleic acid (RNA). The polynucleotide may be any synthetic nucleic acid known in the art, such as peptide nucleic acid (PNA), glycerol nucleic acid (GNA), threose nucleic acid (TNA), locked nucleic acid (LNA), morpholino nucleic acid or other synthetic polymers with nucleotide side chains. The polynucleotide may comprise any of the nucleotides discussed above, including the modified nucleotides.

The target polynucleotide is preferably from about 15 to about 30 nucleotides in length, such as from about 20 to about 25 nucleotides in length. For example, the polynucleotide can be about 15, about 16, about 17, about 18, about 19, about 20, about 21, about 22, about 23, about 24, about 25, about 26, about 27, about 28, about 29 or about 30 nucleotides in length.

The group of two or more target polynucleotides may be any group of polynucleotides. For instance, the group may be associated with a particular phenotype. The group may be associated with a particular type of cell. For instance, the group may be indicative of a bacterial cell. The group may be indicative of a virus, a fungus or a parasite.

The target polynucleotide is preferably a microRNA (or miRNA). The group of two or more target polynucleotides is preferably a group of two or more miRNAs. Suitable miRNAs for use in the invention are well known in the art. For instance, suitable miRNAs are stored on publically available databases (Jiang Q., Wang Y., Hao Y., Juan L., Teng M., Zhang X., Li M., Wang G., Liu Y., (2009) miR2Disease: a manually curated database for microRNA deregulation in human disease. Nucleic Acids Res.).

The miRNA(s) can preferably be used to diagnose or prognose a disease or condition. The disease or condition is preferably cancer, coronary heart disease, cardiovascular disease or sepsis. The disease or condition is more preferably abdominal aortic aneurysm, acute lymphoblastic leukemia (ALL), acute myeloid leukemia (AML), acute myocardial infarction, acute promyelocytic leukemia (APL), adenoma, adrenocortical carcinoma, alcoholic liver disease, Alzheimer's disease, anaplastic thyroid carcinoma (ATC), anxiety disorder, asthma, astrocytoma, atopic dermatitis, autism spectrum disorder (ASD), B-cell chronic lymphocytic leukemia, B-cell lymphoma, Becker muscular dystrophy (BMD), bladder cancer, brain neoplasm, breast cancer, Burkitt lymphoma, cardiac hypertrophy, cardiomyopathy, cardiovascular disease, cerebellar neurodegeneration, cervical cancer, cholangiocarcinoma, cholesteatoma, choriocarcinoma, chronic lymphocytic leukemia, chronic myeloid leukemia, chronic pancreatitis, colon carcinoma, colorectal cancer, congenital heart disease, coronary artery disease, cowden syndrome, dermatomyositis (DM), diabetic nephropathy, diarrhea predominant irritable bowel syndrome, diffuse large B-cell lymphoma, dilated cardiomyopathy, down syndrome (DS), duchenne muscular dystrophy (DMD), endometrial cancer, endometrial endometrioid adenocarcinoma, endometriosis, epithelial ovarian cancer, esophageal cancer, esophagus squamous cell carcinoma, essential thrombocythemia (ET), facioscapulohumeral muscular dystrophy (FSHD), follicular lymphoma (FL), follicular thyroid carcinoma (FTC), frontotemporal dementia, gastric cancer (stomach cancer), glioblastoma, glioblastoma multiforme (GBM), glioma, glomerular disease, glomerulosclerosis, hamartoma, HBV-related cirrhosis, HCV infection, head and neck cancer, head and neck squamous cell carcinoma (HNSCC), hearing loss, heart disease, heart failure, hepatitis B, hepatitis C, hepatocellular carcinoma (HCC), hilar cholangiocarcinoma, Hodgkin's lymphoma, homozygous sickle cell disease (HbSS), Huntington's disease (HD), hypertension, hypopharyngeal cancer, inclusion body myositis (IBM), insulinoma, intrahepatic cholangiocarcinoma (ICC), kidney cancer, kidney disease, laryngeal carcinoma, late insomnia (sleep disease), leiomyoma of lung, leukemia, limb-girdle muscular dystrophies types 2A (LGMD2A), lipoma, lung adenocarcinoma, lung cancer, lymphoproliferative disease, malignant lymphoma, malignant melanoma, malignant mesothelioma (MM), mantle cell lymphoma (MCL), medulloblastoma, melanoma, meningioma, metabolic disease, miyoshi myopathy (MM), multiple myeloma (MM), multiple sclerosis, MYC-rearranged lymphoma, myelodysplastic syndrome, myeloproliferative disorder, myocardial infarction, myocardial injury, myoma, nasopharyngeal carcinoma (NPC), nemaline myopathy (NM), nephritis, neuroblastoma (NB), neutrophilia, Niemann-Pick type C (NPC) disease, non-alcoholic fatty liver disease (NAFLD), non-small cell lung cancer (NSCLC), obesity, oral carcinomaosteosarcoma ovarian cancer (OC), pancreatic cancer, pancreatic ductal adenocarcinoma (PDAC), pancreatic neoplasia, panic disease, papillary thyroid carcinoma (PTC), Parkinson's disease, PFV-1 infection, pharyngeal disease, pituitary adenoma, polycystic kidney disease, polycystic liver disease, polycythemia vera (PV), polymyositis (PM), primary biliary cirrhosis (PBC), primary myelofibrosis, prion disease, prostate cancer, psoriasic arthritis, psoriasis, pulmonary hypertension, recurrent ovarian cancer, renal cell carcinoma, renal clear cell carcinoma, retinitis pigmentosa (RP), retinoblastoma, rhabdomyosarcoma, rheumatic heart disease and atrial fibrillation, rheumatoid arthritis, sarcoma, schizophrenia, sepsis, serous ovarian cancer, Sezary syndrome, skin disease, small cell lung cancer, spinocerebellar ataxia, squamous carcinoma, T-cell leukemia, teratocarcinoma, testicular germ cell tumor, thalassemia, thyroid cancer, tongue squamous cell carcinoma, tourette's syndrome, type 2 diabetes, ulcerative colitis (UC), uterine leiomyoma (ULM), uveal melanoma, vascular disease, vesicular stomatitis or Waldenstrom macroglobulinemia (WM). Since the multiplex method of the invention may determine the presence of absence of two or more miRNAs, it is possible to prognose or diagnose two or more of any of the diseases listed above.

The group of two or more analytes may be any group of analytes. For instance, the group may be associated with a particular phenotype. The group may be associated with a particular type of cell. For instance, the group may be indicative of a bacterial cell. The group may be indicative of a virus, a fungus or a parasite. The group may be a specific panel of recreational drugs (such as the SAMHSA 5 panel test), of explosives or of environmental pollutants.

The group of two or more analytes is preferably a group of two or more biomarkers that can be used to diagnose or prognose a disease or condition. The biomarkers may be any of the analytes mentioned above, such as proteins or polynucleotides. Suitable panels of biomarkers are known in the art, for example as described in Edwards, A. V. G. et al. (2008) *Mol. Cell. Proteomics* 7, p 1824-183'7; Jacquet, S. et al. (2009), *Mol. Cell. Proteomics* 8, p 2687-2699; Anderson N. L. et al (2010) *Clin. Chem.* 56, 177-185. The disease or condition is preferably cancer, coronary heart disease, cardiovascular disease or sepsis.

The group may comprise two or more analytes in the same class. Analytes are within the same class if they have structural similarity. If the analytes are proteins, they are within the same class if they are in the same Structural Classification of Proteins (SCOP) classification. Analytes are within the same class if they related functionally or related phylogenetically. For instance, the opiates, such as heroin, codeine and morphine, may be considered to be in the same class of analytes. Similarly, the different forms of interleukin 1, such as IL-1α, IL-1β and IL-1RA, may be considered to be in same class of analytes. In the context of the invention, a class of analytes is typically two or more analytes that are different structurally but can be bound by one aptamer. The method preferably comprises the use of at least one probe which comprises an aptamer that binds to the analyte members in a class. For instance, such an embodiment allows the determination of the presence or absence or one or more IL-1 analytes in a sample. The ability to detect the presence or absence of one or more analyte members in a particular class has its advantages. For instance, an initial multiplex assay may be carried out for a variety of classes of analytes. Once the presence of one more classes has been determined, more specific multiplex assays relating to those classes may be carried out to determine the presence or absence of one or more of the analyte members within each class.

Transmembrane Pore

A transmembrane pore is a structure that crosses the membrane to some degree. It permits hydrated ions driven by an applied potential to flow across or within the membrane. The transmembrane pore typically crosses the entire membrane so that hydrated ions may flow from one side of the membrane to the other side of the membrane. However, the transmembrane pore does not have to cross the membrane. It may be closed at one end. For instance, the pore may be a well in the membrane along which or into which hydrated ions may flow.

Any membrane may be used in accordance with the invention. Suitable membranes are well-known in the art. The membrane is preferably an amphiphilic layer. An amphiphilic layer is a layer formed from amphiphilic molecules, such as phospholipids, which have both at least one hydrophilic portion and at least one lipophilic or hydrophobic portion. The amphiphilic molecules may be synthetic or naturally occurring. Non-naturally occurring amphiphiles and amphiphiles which form a monolayer are known in the art and include, for example, block copolymers (Gonzalez-Perez et al., Langmuir, 2009, 25, 10447-10450). Block copolymers are polymeric materials in which two or more monomer sub-units are polymerized together to create a single polymer chain. Block copolymers typically have properties that are contributed by each monomer sub-unit. However, a block copolymer may have unique properties that polymers formed from the individual sub-units do not possess. Block copolymers can be engineered such that one of the monomer sub-units is hydrophobic (i.e. lipophilic), whilst the other sub-unit(s) are hydrophilic whilst in aqueous media. In this case, the block copolymer may possess amphiphilic properties and may form a structure that mimics a biological membrane. The block copolymer may be a diblock (consisting of two monomer sub-units), but may also be constructed from more than two monomer sub-units to form more complex arrangements that behave as amphipiles. The copolymer may be a triblock, tetrablock or pentablock copolymer.

The amphiphilic layer is typically a planar lipid bilayer or a supported bilayer.

The amphiphilic layer is typically a lipid bilayer. Lipid bilayers are models of cell membranes and serve as excellent platforms for a range of experimental studies. For example, lipid bilayers can be used for in vitro investigation of membrane proteins by single-channel recording. Alternatively, lipid bilayers can be used as biosensors to detect the presence of a range of substances. The lipid bilayer may be any lipid bilayer. Suitable lipid bilayers include, but are not limited to, a planar lipid bilayer, a supported bilayer or a liposome. The lipid bilayer is preferably a planar lipid bilayer. Suitable lipid bilayers are disclosed in International Application No. PCT/GB08/000563 (published as WO 2008/102121), International Application No. PCT/GB08/004127 (published as WO 2009/077734) and International Application No. PCT/GB2006/001057 (published as WO 2006/100484).

Methods for forming lipid bilayers are known in the art. Suitable methods are disclosed in the Examples. Lipid bilayers are commonly formed by the method of Montal and Mueller (Proc. Natl. Acad. Sci. USA., 1972; 69: 3561-3566), in which a lipid monolayer is carried on aqueous solution/air interface past either side of an aperture which is perpendicular to that interface.

The method of Montal & Mueller is popular because it is a cost-effective and relatively straightforward method of forming good quality lipid bilayers that are suitable for protein pore insertion. Other common methods of bilayer formation include tip-dipping, painting bilayers and patch-clamping of liposome bilayers.

In a preferred embodiment, the lipid bilayer is formed as described in International Application No. PCT/GB08/004127 (published as WO 2009/077734).

In another preferred embodiment, the membrane is a solid state layer. A solid-state layer is not of biological origin. In other words, a solid state layer is not derived from or isolated from a biological environment such as an organism or cell, or a synthetically manufactured version of a biologically available structure. Solid state layers can be formed from both organic and inorganic materials including, but not limited to, microelectronic materials, insulating materials such as $Si_3N_4$, $Al_2O_3$, and SiO, organic and inorganic polymers such as polyamide, plastics such as Teflon® or elastomers such as two-component addition-cure silicone rubber, and glasses. The solid state layer may be formed from monatomic layers, such as graphene, or layers that are only a few atoms thick. Suitable graphene layers are disclosed in International Application No. PCT/US2008/010637 (published as WO 2009/035647). An amphiphilic layer may be formed across a solid state pore. This may be described in the art as hybrid pore formation (Hall et al., Nat Nanotechnol., 2010, 5, 874-877). The method is typically carried out using (i) an artificial amphiphilic layer comprising a pore, (ii) an isolated, naturally-occurring lipid bilayer comprising a pore, or (iii) a cell having a pore inserted therein. The method is typically carried out using an artificial amphiphilic layer, such as an artificial lipid bilayer. The layer may comprise other transmembrane and/or intramembrane proteins as well as other molecules in addition to the pore. Suitable apparatus and conditions are discussed below. The method of the invention is typically carried out in vitro.

If one probe is used, the probe is preferably coupled to the membrane, for example as described in PCT/GB12/051191. If a panel of two or more probes is used, one or more of the probes in the panel are preferably coupled to the membrane. Each probe in the panel is more preferably coupled to the membrane. This may be done using any known method. If the membrane is an amphiphilic layer, such as a lipid bilayer (as discussed in detail above), a probe is preferably coupled to the membrane via a polypeptide present in the membrane or a hydrophobic anchor present in the membrane. The hydrophobic anchor is preferably a lipid, fatty acid, sterol, carbon nanotube or amino acid.

A probe may be coupled directly to the membrane. A probe is preferably coupled to the membrane via a linker. Preferred linkers include, but are not limited to, polymers, such as polynucleotides, polyethylene glycols (PEGs) and polypeptides.

The coupling may be stable or transient. For certain applications, the transient nature of the coupling is preferred. Transient coupling minimises permanent blocking allowing data to be accumulated more quickly as time is not lost in manually unblocking the pore. When permanent coupling is used the amphiphilic layer may be destabilized or it could cause the build up of tethered probes on the cis side, thus altering the experimental equilibrium. These effects can be minimised by coupling transiently. Chemical groups that form stable or transient links with the membrane are discussed in more detail below. A probe may be transiently coupled to an amphiphilic layer, such as a lipid bilayer using cholesterol or a fatty acyl chain. Any fatty acyl chain having a length of from about 6 to about 30 carbon atoms, such as hexadecanoic acid, may be used.

In preferred embodiments, one or more probes are or each probe is coupled to an amphiphilic layer. Coupling to synthetic lipid bilayers has been carried out previously with various different tethering strategies. These are summarised in Table 1 below.

TABLE 1

| Attachment group | Type of coupling | Reference |
|---|---|---|
| Thiol | Stable | Yoshina-Ishii, C. and S. G. Boxer (2003). "Arrays of mobile tethered vesicles on supported lipid bilayers." *J Am Chem Soc* 125(13): 3696-7. |
| Biotin | Stable | Nikolov, V., R. Lipowsky, et al. (2007). "Behavior of giant vesicles with anchored DNA molecules." *Biophys J* 92(12): 4356-68 |
| Cholestrol | Transient | Pfeiffer, I. and F. Hook (2004). "Bivalent cholesterol-based coupling of oligonucletides to lipid membrane assemblies." *J Am Chem Soc* 126(33): 10224-5 |
| Lipid | Stable | van Lengerich, B., R. J. Rawle, et al. "Covalent attachment of lipid vesicles to a fluid-supported bilayer allows observation of DNA-mediated vesicle interactions." *Langmuir* 26(11): 8666-72 |

Probes may be functionalized using a modified phosphoramidite in the synthesis reaction, which is easily compatible for the addition of reactive groups, such as thiol, cholesterol, lipid and biotin groups. These different attachment chemistries give a suite of attachment options for probes. Each different modification group tethers the probe in a slightly different way and coupling is not always permanent so giving different dwell times for the probe to the bilayer.

Coupling of probes can also be achieved by a number of other means provided that a reactive group can be added to the probe. The addition of reactive groups to either end of DNA has been reported previously. A thiol group can be added to the 5' of ssDNA using polynucleotide kinase and ATPγS (Grant, G. P. and P. Z. Qin (2007). "A facile method for attaching nitroxide spin labels at the 5' terminus of nucleic acids." Nucleic Acids Res 35(10): e77). A more diverse selection of chemical groups, such as biotin, thiols and fluorophores, can be added using terminal transferase to incorporate modified oligonucleotides to the 3' of ssDNA (Kumar, A., P. Tchen, et al. (1988). "Nonradioactive labeling of synthetic oligonucleotide probes with terminal deoxynucleotidyl transferase." Anal Biochem 169(2): 376-82).

Alternatively, the reactive group could be considered to be the addition of a short piece of DNA complementary to one already coupled to the bilayer, so that attachment can be achieved via hybridisation. Ligation of short pieces of ssDNA have been reported using T4 RNA ligase I (Troutt, A. B., M. G. McHeyzer-Williams, et al. (1992). "Ligation-anchored PCR: a simple amplification technique with single-sided specificity." Proc Natl Acad Sci USA 89(20): 9823-5). Alternatively either ssDNA or dsDNA could be ligated to native dsDNA and then the two strands separated by thermal or chemical denaturation. To native dsDNA, it is possible to add either a piece of ssDNA to one or both of the ends of the duplex, or dsDNA to one or both ends. Then, when the duplex is melted, each single strand will have either a 5' or 3' modification if ssDNA was used for ligation or a modification at the 5' end, the 3' end or both if dsDNA was used for ligation. If the probe contains a synthetic polynucleotide, the coupling chemistry can be incorporated during the chemical synthesis of the probe. For instance, the probe can be synthesized using a primer with a reactive group attached to it.

A common technique for the amplification of sections of genomic DNA is using polymerase chain reaction (PCR). In this technique, using two synthetic oligonucleotide primers, a number of copies of the same section of DNA can be generated, where for each copy the 5' end of each strand in the duplex will be a synthetic polynucleotide. By using an antisense primer that has a reactive group, such as a cholesterol, thiol, biotin or lipid, each copy of the target DNA amplified will contain a reactive group for coupling.

If the pore is a transmembrane protein pore as discussed below, the probe or one or more probes are preferably not coupled to the pore. If the pore is a protein pore, the probe or the probes in the panel are more preferably not covalently attached to the pore.

The barrel or channel of the pore (through which hydrated ions flow) may have any width. The barrel or channel typically has more than one width, i.e. the width of the barrel or channel may change along its length. The pore has a narrowest part, known in the art as the constriction site. This is the narrowest part of the barrel or channel. The location of the narrowest part can be determined using any method known in the art. The narrowest part of a protein pore may be identified using protein modelling, x-ray diffraction measurement of the protein in a crystalline state (Rupp B (2009). Biomolecular Crystallography: Principles, Practice and Application to Structural Biology. New York: Garland Science.), nuclear magnetic resonance (NMR) spectroscopy of the protein in solution (Mark Rance; Cavanagh, John; Wayne J. Fairbrother; Arthur W. Hunt III; Skelton, Nicholas J. (2007). Protein NMR spectroscopy: principles and practice (2nd ed.). Boston: Academic Press.) or cryo-electron microscopy of the protein in a frozen-hydrated state (van Heel M, Gowen B, Matadeen R, Orlova E V, Finn R, Pape T, Cohen D, Stark H, Schmidt R, Schatz M, Patwardhan A (2000). "Single-particle electron cryo-microscopy: towards atomic resolution". Q Rev Biophys. 33: 307-69. Structural information of proteins determined by above mentioned methods are publicly available from the protein bank (PDB) database.

Protein modelling exploits the fact that protein structures are more conserved than protein sequences amongst homologues. Hence, producing atomic resolution models of proteins is dependent upon the identification of one or more protein structures that are likely to resemble the structure of the query sequence. In order to assess whether a suitable protein structure exists to use as a "template" to build a protein model, a search is performed on the protein data bank (PDB) database. A protein structure is considered a suitable template if it shares a reasonable level of sequence identity with the query sequence. If such a template exists, then the template sequence is "aligned" with the query sequence, i.e. residues in the query sequence are mapped onto the template residues. The sequence alignment and template structure are then used to produce a structural model of the query sequence. Hence, the quality of a protein model is dependent upon the quality of the sequence alignment and the template structure.

The narrowest part of the pore is sufficiently narrow that the quadruplex formed by sequence (ii) cannot enter. Quadruplexes are discussed in more detail below. The narrowest part of the pore is also sufficiently wide that the region (iii) can enter it and affect the current flowing through the pore. As discussed in more detail below, the region preferably comprises a polymer. The narrowest part of the pore is sufficiently wide that the polymer can enter it and affect the current flowing through the pore. In some instances, the region can comprise a polynucleotide. The narrowest part of the pore is preferably sufficiently narrow that a single stranded polynucleotide can enter and pass through the pore, but a double-stranded polynucleotide cannot enter and pass through the pore. Typically the narrowest part of the pore is sufficiently wide to permit ssDNA or RNA to enter it or translocate it, but sufficiently narrow that a quadruplex cannot.

The transmembrane pore is preferably a transmembrane protein pore. A transmembrane protein pore is a polypeptide or a collection of polypeptides that permits hydrated ions to flow from one side of a membrane to the other side of the membrane. In the present invention, the transmembrane protein pore is capable of forming a pore that permits hydrated ions driven by an applied potential to flow from one side of the membrane to the other. The transmembrane protein pore preferably permits analytes, such as nucleotides, to flow from one side of the membrane, such as a lipid bilayer, to the other. The transmembrane protein pore allows a polypeptide or a polynucleotide, such as DNA or RNA, to be moved through the pore.

The transmembrane protein pore may be a monomer or an oligomer. The pore is preferably made up of several repeating subunits, such as 6, 7, 8 or 9 subunits. The pore is preferably a hexameric, heptameric, octameric or nonameric pore.

The transmembrane protein pore typically comprises a barrel or channel through which the ions may flow. The subunits of the pore typically surround a central axis and contribute strands to a transmembrane β barrel or channel or a transmembrane α-helix bundle or channel.

The barrel or channel of the transmembrane protein pore typically comprises amino acids that facilitate interaction with the region (iii), such as polymer units in the region. These amino acids are preferably located at or near the narrowest part of the pore, such as at or near a constriction of the barrel or channel. The transmembrane protein pore typically comprises one or more positively charged amino acids, such as arginine, lysine or histidine, or aromatic amino acids, such as tyrosine or tryptophan. These amino acids typically facilitate the interaction between the pore and negatively-charged polymer units, such as nucleotides, in the region (iii).

Transmembrane protein pores for use in accordance with the invention can be derived from β-barrel pores or α-helix bundle pores. β-barrel pores comprise a barrel or channel that is formed from β-strands. Suitable β-barrel pores include, but are not limited to, β-toxins, such as α-hemolysin, anthrax toxin and leukocidins, and outer membrane proteins/porins of bacteria, such as *Mycobacterium smegmatis* porin (Msp), for example MspA, MspB or MspC, lysenin, outer membrane phospholipase A and *Neisseria* autotransporter lipoprotein (NalP). α-helix bundle pores comprise a barrel or channel that is formed from α-helices. Suitable α-helix bundle pores include, but are not limited to, inner membrane proteins and a outer membrane proteins, such as WZA and ClyA toxin. The transmembrane pore may be derived from lysenin. Suitable pores derived from lysenin are disclosed in International Application No. PCT/GB2013/050667 (published as WO 2013/153359). The transmembrane pore is preferably derived from α-hemolysin (α-HL) or leukocidin.

The pore may be a homo-oligomer (all monomer units identical) or a hetero-oligomer (two or more different types of monomer). The pore may comprise linked monomers, for example dimers.

The pore may comprise at least one dimer and 1, 2, 3, 4, 5, 6, 7 or 8 monomers. The pore may comprise two, three, four or more dimers. Such pores further comprise sufficient monomers to form the pore. A further pore comprises only dimers, for example a pore may comprise 4, 5, 6, 7 or 8 dimers. A specific pore according to the inventions comprises four dimers. The dimers may oligomerise into a pore with a structure such that only one monomer of a dimer contributes to the barrel or vestibule of the pore. Typically the other monomers of the construct will be on the outside of the barrel or vestibule of the pore. For example, a pore may comprise 5, 6, 7 or 8 dimers where the barrel or vestibule comprises 8 monomers.

The transmembrane protein pore is preferably derived from α-hemolysin (α-HL). The wild type α-HL pore is formed of seven identical monomers or subunits (i.e. it is heptameric). The transmembrane protein pore preferably comprises seven monomers derived from α-HL. The sequence of one monomer or subunit of α-hemolysin-NN (i.e. a pore derived from α-HL) is shown in SEQ ID NO: 2. α-hemolysin-NN contains the substitutions E111N and K147N. The transmembrane protein pore preferably comprises seven monomers each comprising the sequence shown in SEQ ID NO: 2 or a variant thereof. Amino acids 1, 7 to 21, 31 to 34, 45 to 51, 63 to 66, 72, 92 to 97, 104 to 111, 124 to 136, 149 to 153, 160 to 164, 173 to 206, 210 to 213, 217, 218, 223 to 228, 236 to 242, 262 to 265, 272 to 274, 287 to 290 and 294 of SEQ ID NO: 4 form loop regions. Residues 113 and 147 of SEQ ID NO: 2 form part of a constriction of the barrel or channel of α-HL.

The pore preferably comprises seven proteins or monomers each comprising the sequence shown in SEQ ID NO: 2 or a variant thereof. The transmembrane protein is preferably (a) formed of seven identical subunits as shown in SEQ ID NO: 2 or (b) a variant thereof in which one or more of, or all of, the seven subunits is a variant of SEQ ID NO: 2 and which retains pore activity. 1, 2, 3, 4, 5, 6 or 7 of the subunits may be variants. The variants in a pore may be the same of different. The seven subunits may be the same (homoheptamer) or different (heteroheptamer).

A variant of SEQ ID NO: 2 is a protein that has an amino acid sequence which varies from that of SEQ ID NO: 2 and which retains its pore forming ability. The ability of a variant to form a pore can be assayed using any method known in the art. For instance, the variant may be inserted into an amphiphilic layer, such as a lipid bilayer, along with other appropriate subunits and its ability to oligomerise to form a pore may be determined. Methods are known in the art for inserting subunits into amphiphilic layers, such as lipid bilayers. For example, subunits may be suspended in a purified form in a solution containing a lipid bilayer such that it diffuses to the lipid bilayer and is inserted by binding to the lipid bilayer and assembling into a functional state. Alternatively, subunits may be directly inserted into the membrane using the "pick and place" method described in M. A. Holden, H. Bayley. J. Am. Chem. Soc. 2005, 127, 6502-6503 and International Application No. PCT/GB2006/001057 (published as WO 2006/100484).

One preferred variant of SEQ ID NO: 2 is the wild-type subunit, i.e. a subunit in which E has been replaced at position 111 and K has been replaced at position 147.

The variant may include modifications that facilitate covalent attachment to or interaction with another molecule. The variant preferably comprises one or more reactive cysteine residues that facilitate attachment. For instance, the variant may include a cysteine at one or more of positions 8, 9, 17, 18, 19, 44, 45, 50, 51, 237, 239 and 287 and/or on the amino or carboxy terminus of SEQ ID NO: 2. Preferred variants comprise a substitution of the residue at position 8, 9, 17, 237, 239 and 287 of SEQ ID NO: 2 with cysteine (A8C, T9C, N17C, K237C, S239C or E287C). The variant is preferably any one of the variants described in International Application No. PCT/GB09/001690 (published as WO 2010/004273), PCT/GB09/001679 (published as WO 2010/004265) or PCT/GB10/000133 (published as WO 2010/086603).

The variant may also include modifications that facilitate any interaction with polymer units in the probe, such as nucleotides, amino acids or ethylene oxide.

The variant may be a naturally occurring variant which is expressed naturally by an organism, for instance by a *Staphylococcus* bacterium. Alternatively, the variant may be expressed in vitro or recombinantly by a bacterium such as *Escherichia coli*. Variants also include non-naturally occurring variants produced by recombinant technology.

Over the entire length of the amino acid sequence of SEQ ID NO: 2, a variant will preferably be at least 50% homologous to that sequence based on amino acid identity. More preferably, the variant may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 2 over the entire sequence. There may be at least 80%, for example at least 85%, 90% or 95%, amino acid identity over a stretch of 200 or more, for example 230, 250, 270 or 280 or more, contiguous amino acids ("hard homology").

Standard methods in the art may be used to determine homology. For example the UWGCG Package provides the BESTFIT program which can be used to calculate homology, for example used on its default settings (Devereux et al (1984) *Nucleic Acids Research* 12, p 387-395). The PILEUP and BLAST algorithms can be used to calculate homology or line up sequences (such as identifying equivalent residues or corresponding sequences (typically on their default settings)), for example as described in Altschul S. F. (1993) J Mol Evol 36:290-300; Altschul, S. F et al (1990) J Mol Biol 215:403-10. Software for performing BLAST analyses is publicly available through the National Center for Biotechnology Information (http://www.ncbi.nlm.nih.gov/).

Amino acid substitutions may be made to the amino acid sequence of SEQ ID NO: 2 in addition to those discussed above, for example up to 1, 2, 3, 4, 5, 10, 20 or 30 substitutions. Conservative substitutions replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative substitution may introduce another amino acid that is aromatic or aliphatic in the place of a pre-existing aromatic or aliphatic amino acid. Conservative amino acid changes are well-known in the art and may be selected in accordance with the properties of the 20 main amino acids as defined in Table 2 below. Where amino acids have similar polarity, this can also be determined by reference to the hydropathy scale for amino acid side chains in Table 3.

TABLE 2

| Chemical properties of amino acids | |
|---|---|
| Ala | aliphatic, hydrophobic, neutral |
| Cys | polar, hydrophobic, neutral |
| Asp | polar, hydrophilic, charged (−) |
| Glu | polar, hydrophilic, charged (−) |
| Phe | aromatic, hydrophobic, neutral |
| Gly | aliphatic, neutral |
| His | aromatic, polar, hydrophilic, charged (+) |
| Ile | aliphatic, hydrophobic, neutral |
| Lys | polar, hydrophilic, charged(+) |
| Leu | aliphatic, hydrophobic, neutral |
| Met | hydrophobic, neutral |
| Asn | polar, hydrophilic, neutral |
| Pro | hydrophobic, neutral |
| Gln | polar, hydrophilic, neutral |
| Arg | polar, hydrophilic, charged (+) |
| Ser | polar, hydrophilic, neutral |
| Thr | polar, hydrophilic, neutral |
| Val | aliphatic, hydrophobic, neutral |
| Trp | aromatic, hydrophobic, neutral |
| Tyr | aromatic, polar, hydrophobic |

TABLE 3

| Hydropathy scale | |
|---|---|
| Side Chain | Hydropathy |
| Ile | 4.5 |
| Val | 4.2 |
| Leu | 3.8 |
| Phe | 2.8 |
| Cys | 2.5 |
| Met | 1.9 |

TABLE 3-continued

Hydropathy scale

| Side Chain | Hydropathy |
|---|---|
| Ala | 1.8 |
| Gly | −0.4 |
| Thr | −0.7 |
| Ser | −0.8 |
| Trp | −0.9 |
| Tyr | −1.3 |
| Pro | −1.6 |
| His | −3.2 |
| Glu | −3.5 |
| Gln | −3.5 |
| Asp | −3.5 |
| Asn | −3.5 |
| Lys | −3.9 |
| Arg | −4.5 |

One or more amino acid residues of the amino acid sequence of SEQ ID NO: 2 may additionally be deleted from the polypeptides described above. Up to 1, 2, 3, 4, 5, 10, 20 or 30 residues may be deleted, or more.

Variants may include fragments of SEQ ID NO: 2. Such fragments retain pore forming activity. Fragments may be at least 50, 100, 200 or 250 amino acids in length. Such fragments may be used to produce the pores. A fragment preferably comprises the pore forming domain of SEQ ID NO: 2. Fragments typically include residues 119, 121, 135. 113 and 139 of SEQ ID NO: 2.

One or more amino acids may be alternatively or additionally added to the polypeptides described above. An extension may be provided at the amino terminal or carboxy terminal of the amino acid sequence of SEQ ID NO: 2 or polypeptide variant or fragment thereof. The extension may be quite short, for example from about 1 to about 10 amino acids in length. Alternatively, the extension may be longer, for example up to about 50 or about 100 amino acids. A carrier protein may be fused to an amino acid sequence according to the invention.

As discussed above, a variant is a polypeptide that has an amino acid sequence which varies from that of SEQ ID NO: 2 and which retains its ability to form a pore. A variant typically contains the regions of SEQ ID NO: 2 that are responsible for pore formation. The pore forming ability of α-HL, which contains a β-barrel, is provided by β-strands in each subunit. A variant of SEQ ID NO: 2 typically comprises the regions in SEQ ID NO: 2 that form β-strands. The amino acids of SEQ ID NO: 2 that form β-strands are discussed above. One or more modifications can be made to the regions of SEQ ID NO: 2 that form β-strands as long as the resulting variant retains its ability to form a pore. Specific modifications that can be made to the β-strand regions of SEQ ID NO: 2 are discussed above.

A variant of SEQ ID NO: 2 preferably includes one or more modifications, such as substitutions, additions or deletions, within its α-helices and/or loop regions. Amino acids that form α-helices and loops are discussed above.

The transmembrane protein pore is also preferably derived from leukocidin. A leukocidin is a hetero-oligomeric pore with two different subunits, one class S subunit and one class F subunit. Suitable leukocidins include, but are not limited to, gamma hemolysin (γ-HL) comprising LukF (HlgB) and Hlg2 (HlgA), leukocidin comprising LukF (HlgB) and LukS(HlgC), leukocidin PV comprising LukF-PV and LukS-PV, LukE/LukD pore comprising LukE and LukD and LukS-I/LukF-I comprising LukF-I and LukS-I.

When the transmembrane protein pore is a leukocidin, it is preferably derived from gamma hemolysin (γ-HL). The wild type γ-HL pore is formed of eight subunits (i.e. it is octameric) and contains four subunits of LukF and four subunits of Hlg2. The sequence of one monomer or subunit of LukF is shown in shown in SEQ ID NO: 4. The sequence of one monomer or subunit of Hlg2 is shown in SEQ ID NO: 6. The transmembrane protein pore preferably comprises four monomers each comprising the sequence shown in SEQ ID NO: 4 or a variant thereof and four monomers each comprising the sequence shown in SEQ ID NO: 6 or a variant thereof. Amino acids 109-147 of SEQ ID NO: 4 and 103-139 of SEQ ID NO: 6 form loop regions.

The γ-hemolysin pore is preferably (a) γ-hemolysin formed of four identical subunits as shown in SEQ ID NO: 4 and four identical subunits as shown in SEQ ID NO: 6 or (b) a variant thereof in which one or more of, or all of, the subunits is a variant of SEQ ID NO: 4 and/or one or more of, or all of, the subunits is a variant of SEQ ID NO: 6 and the pore retains pore activity. Such pores are hetero-octamers. 1, 2, 3 or 4 of the subunits may be variants of SEQ ID NO: 4 and/or 6. The variants in a pore may be the same of different.

A variant of SEQ ID NO: 4 or 6 is a protein that has an amino acid sequence which varies from that of SEQ ID NO: 4 or 6 and which retains its pore forming ability. The ability of a variant to form a pore can be assayed using any method known in the art. For instance, the variant may be inserted into an amphiphilic layer, such as a lipid bilayer, along with other appropriate subunits and its ability to oligomerise to form a pore may be determined. Methods are known in the art for inserting subunits into amphiphilic layers, such as lipid bilayers. Suitable methods are discussed above.

The variant may include modifications that facilitate covalent attachment to or interaction with another molecule. The variant preferably comprises one or more reactive cysteine residues that facilitate attachment. The variant may also include modifications that facilitate any interaction with polymer units in the probe, such as nucleotides, amino acids or ethylene oxide.

The variant may be a naturally occurring variant which is expressed naturally by an organism, for instance by a *Staphylococcus* bacterium. Alternatively, the variant may be expressed in vitro or recombinantly by a bacterium such as *Escherichia coli*. Variants also include non-naturally occurring variants produced by recombinant technology. Over the entire length of the amino acid sequence of SEQ ID NO: 4 or 6, a variant will preferably be at least 50% homologous to that sequence based on amino acid identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 4 or 6 over the entire sequence. There may be at least 80%, for example at least 85%, 90% or 95%, amino acid identity over a stretch of 200 or more, for example 230, 250, 270 or 280 or more, contiguous amino acids ("hard homology"). Homology can be determined as discussed above.

Amino acid substitutions may be made to the amino acid sequence of SEQ ID NO: 4 or 6 in addition to those discussed above, for example up to 1, 2, 3, 4, 5, 10, 20 or 30 substitutions. Conservative substitutions may be made as discussed above.

One or more amino acid residues of the amino acid sequence of SEQ ID NO: 4 or 6 may additionally be deleted from the polypeptides described above. Up to 1, 2, 3, 4, 5, 10, 20 or 30 residues may be deleted, or more.

Variants may be fragments of SEQ ID NO: 4 or 6. Such fragments retain pore-forming activity. Fragments may be at least 50, 100, 200 or 250 amino acids in length. A fragment preferably comprises the pore-forming domain of SEQ ID NO: 4 or 6.

One or more amino acids may be alternatively or additionally added to the polypeptides described above. An extension may be provided at the amino terminus or carboxy terminus of the amino acid sequence of SEQ ID NO: 4 or 6 or a variant or fragment thereof. The extension may be quite short, for example from about 1 to about 10 amino acids in length. Alternatively, the extension may be longer, for example up to about 50 or about 100 amino acids. A carrier protein may be fused to a pore or variant.

As discussed above, a variant of SEQ ID NO: 4 or 6 is a subunit that has an amino acid sequence which varies from that of SEQ ID NO: 4 or 6 and which retains its ability to form a pore. A variant typically contains the regions of SEQ ID NO: 4 or 6 that are responsible for pore formation. The pore forming ability of γ-HL, which contains a β-barrel, is provided by β-strands in each subunit. A variant of SEQ ID NO: 4 or 6 typically comprises the regions in SEQ ID NO: 4 or 6 that form β-strands. The amino acids of SEQ ID NO: 4 or 6 that form β-strands are discussed above. One or more modifications can be made to the regions of SEQ ID NO: 4 or 6 that form β-strands as long as the resulting variant retains its ability to form a pore. Specific modifications that can be made to the β-strand regions of SEQ ID NO: 4 or 6 are discussed above.

A variant of SEQ ID NO: 4 or 6 preferably includes one or more modifications, such as substitutions, additions or deletions, within its α-helices and/or loop regions. Amino acids that form α-helices and loops are discussed above.

In some embodiments, the transmembrane protein pore is chemically modified. The monomers derived from α-HL (i.e. SEQ ID NO: 2 or a variant thereof) or γ-HL (i.e. SEQ ID NO: 4 or 6 or a variant thereof) may be modified to assist their identification or purification, for example by the addition of histidine residues (a hist tag), aspartic acid residues (an asp tag), a streptavidin tag or a flag tag, or by the addition of a signal sequence to promote their secretion from a cell where the polypeptide does not naturally contain such a sequence. An alternative to introducing a genetic tag is to chemically react a tag onto a native or engineered position on the pore. An example of this would be to react a gel-shift reagent to a cysteine engineered on the outside of the pore. This has been demonstrated as a method for separating α-HL hetero-oligomers (Chem Biol. 1997 July; 4(7):497-505).

The monomer derived from α-HL or γ-HL may be labelled with a revealing label. The revealing label may be any suitable label which allows the pore to be detected. Suitable labels include, but are not limited to, fluorescent molecules, radioisotopes, e.g. $^{125}I$ $^{35}S$, enzymes, antibodies, antigens, polynucleotides and ligands such as biotin.

The monomer derived from α-HL or γ-HL may also be produced using D-amino acids. For instance, the monomer derived from α-HL or γ-HL may comprise a mixture of L-amino acids and D-amino acids. This is conventional in the art for producing such proteins or peptides.

The monomer derived from α-HL or γ-HL may contain one or more specific modifications to facilitate interactions with the probes. The monomer derived from α-HL or γ-HL may also contain other non-specific modifications as long as they do not interfere with pore formation. A number of non-specific side chain modifications are known in the art and may be made to the side chains of the monomer derived from α-HL or γ-HL. Such modifications include, for example, reductive alkylation of amino acids by reaction with an aldehyde followed by reduction with $NaBH_4$, amidination with methylacetimidate or acylation with acetic anhydride.

The monomer derived from α-HL or γ-HL can be produced using standard methods known in the art. The monomer derived from α-HL may be made synthetically or by recombinant means. For example, the pore may be synthesized by in vitro translation and transcription (IVTT). Suitable methods for producing pores are discussed in International Application Nos. PCT/GB09/001690 (published as WO 2010/004273), PCT/GB09/001679 (published as WO 2010/004265) or PCT/GB10/000133 (published as WO 2010/086603). Methods for inserting pores into membranes are discussed.

The pore can be produced using standard methods known in the art. Polynucleotide sequences encoding a pore may be derived and replicated using standard methods in the art. Polynucleotide sequences encoding a pore may be expressed in a bacterial host cell using standard techniques in the art. The pore may be produced in a cell by in situ expression of the polypeptide from a recombinant expression vector. The expression vector optionally carries an inducible promoter to control the expression of the polypeptide. These methods are described in described in Sambrook, J. and Russell, D. (2001). Molecular Cloning: A Laboratory Manual, 3rd Edition. Cold Spring Harbor Laboratory Press, Cold Spring Harbor, N.Y.

The pore may be produced in large scale following purification by any protein liquid chromatography system from protein producing organisms or after recombinant expression. Typical protein liquid chromatography systems include FPLC, AKTA systems, the Bio-Cad system, the Bio-Rad BioLogic system and the Gilson HPLC system.

Probe(s)

The methods of the invention comprise contacting the sample with one or more probes. The uniplex method comprises contacting the sample with one probe. The multiplex method comprises contacting the sample with one probe or a panel of two or more probes. The multiplex method preferably comprises contacting the sample with one probe which comprises two or more repeating units. The multiplex method preferably comprises contacting the sample with a panel of two or more probes, wherein each probe comprises one or more repeating units. For instance, some probes in the panel may comprise one repeating unit while the other probes in the panel may comprise two or more repeating units. Alternatively, all of the probes in the panel may comprise two or more repeating units. The multiplex method most preferably comprises contacting the sample with a panel of two or more probes, wherein each probe in the panel comprises one repeating unit. Each repeating unit specifically recognises one of the target analytes.

The panel may comprise any number of two or more probes, such as 2, 5, 10, 15, 20, 30, 40, 50, 100 or more probes. The panel preferably has from about 4 to about 100 probes, such as from about 5 to about 80 probes, from about 10 to about 60 probes or from about 20 to about 50 probes.

The number of probes used in the multiplex method may be lower than the number of two or more target analytes in the group. For instance, one probe may be used to determine the presence or absence of one or more members of a group of two or more target analytes. In this instance, the probe comprises two or more repeating units. Each repeating unit specifically recognises one of the two or more target analytes.

The number of probes used in the multiplex method may be higher than the number of two or more target analytes in the group. For instance, three probes may be used to determine the presence or absence of one or more members of a group of two analytes. In this instance, one probe may comprise a repeating unit that specifically recognises one of the target analytes and each of the other two probes may comprise repeating units that specifically recognise the other target analyte. The two probes which specifically recognise the same target analyte may be distinguished from each other on the basis of the distinctive currents provided by their respective regions (iii).

The number of probes used in the multiplex method may be equal to the number of two or more target analytes in the group. For instance, three probes may be used to determine the presence or absence of one or more members of a group of three analytes, A, B and C. In this instance, each probe may comprise only one repeating unit and each repeating unit specifically recognises a different target analyte, i.e. A, B or C. This is the simplest embodiment of the invention, but it does not include an internal control.

Alternatively, each probe may comprise two repeating units and each probe may specifically recognise a different combination of target analytes, i.e. AB, AC or BC. This can provide an internal control because positive signals from both probes which recognise B (i.e. AB and BC above) will be required to conclude that B is present in the sample. The repeating units which specifically recognise the same target analyte may be distinguished from each other on the basis of the distinctive currents provided by their respective regions (iii). A skilled person is capable of designing a panel of probes to suit the specific needs of the multiplex method of the invention.

The methods use multiple instances of each or every probe because, if a target analyte is present in the sample, there will almost certainly be multiple instances of the target analyte in the sample. In other words, the methods use multiple instances of the probe or multiple instances of each or every type of probe in the panel of two or more probes.

Each or every member of the group of two or more target analytes is specifically recognised by at least one repeating unit (i.e. at least one type of repeating unit) in the probe (uniplex method) or the panel of two or more probes (multiplex method). As discussed above, two different repeating units may specifically recognise the same target analyte. Two different repeating units which specifically recognise the same target analyte may differ in (i), (ii), (iii), (i) and (ii), (ii) and (iii), (i) and (iii) or (i), (ii) and (iii). If the target analyte is a polynucleotide and the section (i) is a sequence which specifically hybridises to the target polynucleotider, two different repeating units which specifically recognise the same target polynucleotide typically comprise the same section (i) so that they specifically recognise the same target polynucleotide and do not recognise other target polynucleotides.

Each repeating unit specifically recognises only one target analyte. In other words, a repeating unit does not recognise more than one target analyte. A repeating unit specifically recognises a target analyte if it provides a positive signal in the method of the invention when the target analyte is present in the sample. In other words, a repeating unit specifically recognises a target analyte if it affects the current in a distinctive manner when the target analyte is present in the sample. The presence of the analyte is indicated by a change in current resulting from the complex that forms between the section (i) and the target analyte holding a part of the probe, preferably a spacer (iv), in the narrowest part of the pore. Typically, this temporarily results in a steady current flowing through the pore. The identity of the repeating unit (and by association the analyte) is indicated by the distinctive current provided by a region (iii) when the quadruplex formed by sequence (ii) has its braking effect. A repeating unit specifically recognises a target analyte because it comprises a section (i) which specifically binds to the target analyte. The fact that each member is recognised by at least one repeating unit allows the presence or absence of each member in the group to be determined using the multiplex method of the invention. The way in which a repeating unit specifically recognises a target analyte is discussed in more detail below.

Each repeating unit (i.e. each type of repeating unit) in the panel preferably comprises a different section (i). In other words, no two repeating units (i.e. no two types of repeating unit) in the panel comprise the same section (i). Different sections in each repeating unit allows each repeating unit to specifically bind different members of the two or more analytes.

A probe (uniplex method) or repeating unit (multiplex method) comprises at least one sequence (ii). Any number of sequences (ii) may be present in each probe or repeating unit, such as 2, 3, 4, 5, 6, 7, 8, 9, 10 or more. The number of sequences (ii) in each probe or repeating unit is typically identical the number of regions (iii). Each instance of a sequence (ii) and region (iii) typically form a pair. The region (iii) provides a distinctive current as its paired sequence (ii) forms a quadruplex which temporarily holds the region (iii) in the narrowest part of the pore. The sequence (ii) and region (iii) in a pair are typically adjacent to or next to each other in the probe or repeating unit. They may be joined by a linker as discussed in more detail below. Each pair allows the probe or repeating unit (and hence by association the analyte) to be identified. The more pairs present in a probe or repeating unit, the more straightforward it is to identify the probe or repeating unit.

Each probe, repeating unit or pair (i.e. each type of probe, repeating unit or pair) in the panel preferably comprises the same sequence (ii). In other words, all of the probes, repeating units or pairs (i.e. all types of probes, repeating units or pairs) in the panel comprise the same sequence (ii). Each probe, repeating unit or pair may comprise different sequences (ii). Some repeating units may have the same sequence (ii) while others may have different sequences (ii).

A probe (uniplex method) or repeating unit (multiplex method) comprises at least one region (iii). Any number of regions (iii) may be present in each probe or repeating unit, such as 2, 3, 4, 5, 6, 7, 8, 9, 10 or more. The number of regions (iii) in each probe or repeating unit is typically identical the number of sequences (ii). The regions (iii) and sequences (ii) typically form or occur in pairs as discussed above.

Each probe, repeating unit or pair (i.e. each type of probe, repeating unit or pair) in the panel preferably comprises a different region (iii). As discussed in more detail below, the differences between different regions can contribute to the distinctiveness of the effects each probe, repeating unit or pair has on the current flowing through the pore. Two or more repeating units in the panel preferably comprise the same section (i) and different regions (iii). In this embodiment, the distinctiveness of the effects each probe, repeating unit or pair has on the current flowing through pore is typically provided by the differences between the regions. In this embodiment, the two or more repeating units are targeted to the same target analyte because they share the same section (i). This can provide an internal control because positive signals from both probes, repeating units or pairs will be required to conclude that target analyte is present in the sample.

Each probe or repeating unit (i.e. each type of probe or repeating unit) in the panel may comprise a different section (i) and a different region (iii). In other words, no two probes or repeating units (i.e. no two types of probe or repeating unit) in the panel comprise the same section (i) and the same region (iii). In the embodiment, the different probes or repeating units each specifically recognise a different target analyte and the different regions typically contribute to the distinctiveness of the effects each of the two or more probes or repeating units has on the current flowing through pore.

Probe Configuration

Any configuration of probe is envisaged by the invention. The region (iii) may be located between the section (i) and the sequence (ii) capable of forming the quadruplex. The sequence (ii) capable of forming a quadruplex is preferably located between the sequence (i) and the region (iii). A probe may comprise two or more repeating units attached together end to end. Preferred configurations of probe include, but are not limited to, (a) (i)-(ii)-(iii);
(b) [(i)-(ii)-(iii)]x;
(c) (i)-[(ii)-(iii)]x;
(d) (ii)-(iii)-(i);
(e) [(ii)-(iii)-(i)]x;
(f) [(ii)-(iii)]x-(i), where x is any number greater than or equal to 2, such as, 3, 4, 5, 6, 7, 8, 9, 10 or more.

A person skilled in the art is able to design probes suitable for use in the invention. For instance, with knowledge of the dimensions of a pore and the position of its narrowest part, a person skilled in the art is able to design a probe such that region (iii) is held in the narrowest part when the quadruplex formed by the sequence (ii) has its temporary breaking action.

The different parts of the probe or repeating unit, i.e. section (i), sequence (ii) and region (iii), may be attached together directly. The different parts may be attached together by linkers. Such linkers may be helpful to determine the distance between sequence (ii) and region (iii). Any linkers may be used. The linker is preferably a polymer. The polymer is preferably a polynucleotide, a polypeptide or a polyethylene glycol (PEG).

Typically each probe comprises a leader sequence, which leader sequence is the first part of probe to enter into the pore. If sequence (ii) is located between section (i) and region (iii), the leader sequence may be part of region (iii). For instance, region (iii) may have an abasic leader sequence, which leader sequence is the first region of the region (iii) to pass into the pore. If region (iii) is located between sequence (ii) and section (i), the probe may further comprise a leader sequence attached to section (i).

Section (i)

The section (i) specifically binds to the target analyte. This allows the repeating unit to specifically recognise the target analyte and identify its presence or absence in the sample. As discussed above, the complex formed between section (i) and the target analyte temporarily holds a part of the probe in the narrowest part of the pore and this leads to a change in current that can be measured. Typically, it temporarily leads to a steady current flowing through the pore. The level of the steady current may be used to determine the presence or absence of analyte. Typically the steady current level will be lower than the level observed when no analyte is present. A section (i) specifically binds to a target analyte if it results in a detectable or measurable change in current, preferably a detectable or measureable change to a steady current, flowing through the pore in the presence of the target analyte, but does not result in a measurable change in current, preferably a measureable change to a steady current, flowing through the pore in the absence of the target analyte and the presence of other analytes. This can be measured as described in the Examples.

Preferably, the section (i) binds to the target analyte with an affinity that is at least 10 times, such as at least 50, at least 100, at least 200, at least 300, at least 400, at least 500, at least 1000 or at least 10,000 times, greater than its affinity for the other members (i.e. the other target analytes) in the group of two or more analytes. More preferably, the section (i) binds to the target analyte with an affinity that is at least 10 times, such as at least 50, at least 100, at least 200, at least 300, at least 400, at least 500, at least 1000 or at least 10,000 times, greater than its affinity for other analytes. Affinity can be measured using known binding assays, such as those that make use of fluorescence and radioisotopes. Competitive binding assays are also known in the art. The strength of binding between peptides or proteins and polynucleotides can be measured using nanopore force spectroscopy as described in Hornblower et al., Nature Methods. 4: 315-317. (2007).

More preferably, the section (i) does not bind to the other members (i.e. the other target analytes) in the group of two or more analytes except through non-specific interactions, such as hydrophobic interactions, hydrogen bonding, Van der Waal's forces, π-cation interactions and/or electrostatic forces. Most preferably, the section (i) does not bind to any other analyte except through non-specific interactions, such as hydrophobic interactions, hydrogen bonding, Van der Waal's forces, π-cation interactions and/or electrostatic forces.

As discussed above, the binding of section (i) to the target analyte forms a complex that is too big to translocate or move through the pore. This complex acts like a brake which prevents the movement of section (i) through the pore. This braking effect temporarily holds a part of the probe in the narrowest part of pore which results in a change in current flowing through the pore, typically a change to a steady current. The change in current can be measured. The steady current level can be measured. The binding of each probe or repeating unit to its target analyte can therefore be measured in accordance with the invention. The probe or repeating unit is identified using sequence (ii) and region (iii) as discussed in more detail below. After a short while, the complex between section (i) and the target analyte will break down (i.e. section (i) will unbind from the target analyte) under the influence of the applied potential. Free from the braking effect of the complex, section (i) will translocate or move through the pore under the influence of the applied potential.

A person skilled in the art will be able to design sections (i) that specifically bind to the target analyte(s) of interest. If the target analyte is an oligonucleotide or a polynucleotide, suitable sections include, but are not limited to, molecules which bind to their cognate oligonucleotide aptamers; polypeptides which specifically interact with polynucleotides, such as poly-lysine; osmium compounds which specifically interact with methylated DNA; DNA intercalators, such as ethidium bromide; and polynucleotides which specifically hybridise to target oligonucleotides or polynucleotides. Polynucleotide sections (i) are discussed in more detail below.

If the target analyte is a peptide, polypeptide or protein, suitable sections include, but are not limited to, aptamers; polynucleotides which bind to specific polypeptides or proteins, such as DNA elements for transcription factors (e.g. the Rexl promoter which recognizes the homeodomain transcription factor Oxt-4); peptide epitopes for target antibodies or target antibody fragments, such as the haemaglutinin epitope, the FLAG epitope and the Hexa-histidine epitope which are bound by the anti-HA, anti-FLAG and V5 monoclonal antibodies respectively; antibodies or antibody fragments (e.g. Fab or Fc) for target peptides or target proteins; peptide inhibitors of target proteins, such as the protein C inhibitor peptide which forms a specific complex with the Prostate-Specific Antigen (PSA); peptides which form specific binding domains for target proteins, such as the C-terminus of E. coli SSB and leucine zipper domains; specific inhibitor molecules for target proteins, such as sphingosine kinase inhibitor 1, zinc metal ions which interact with PSA and vanadate and pervanadate compound inhibitors of protein tyrosine phosphatases; and specific ligands for target proteins, such fucosylated carbohydrates that serve as ligands for selectins, small oligosaccharides (e.g. galactose) that serve as ligands for lectins, glucose-6-phosphate which is specifically hydrolysed by glucose-6-phosphatase, D-myo-Inositol-1,4,5-triphosphate which interacts with phosphoinositol lipid interacting proteins, maltose which binds to maltose binding protein, digoxigenin which binds to anti-digoxigenin monoclonal antibodies and biotin which binds to streptavidin.

If the target analyte is a small molecule, suitable sections include, but are not limited to, aptamers and peptide or proteins which specifically bind to target small molecules.

Aptamers are small molecules that specifically bind to analytes. Aptamers can be produced using SELEX (Stoltenburg, R. et al., (2007), *Biomolecular Engineering* 24, p 381-403; Tuerk, C. et al., *Science* 249, p 505-510; Bock, L. C. et al., (1992), *Nature* 355, p 564-566) or NON-SELEX (Berezovski, M. et al. (2006), *Journal of the American Chemical Society* 128, p 1410-1411). Aptamers can be designed which bind to one member of the group of two or more analytes, but do not bind to the other members. Apatamers can also be designed which bind to a target analyte, but do not bind to other analytes.

The aptamer is preferably a peptide aptamer or an olignonucleotide aptamer. The peptide aptamer may comprise any amino acids, including non-natural amino acids or modified amino acids. The olignonucleotide aptamer may comprise any nucleotides. The nucleotides may be any of those discussed above.

The aptamer can be any length. The aptamer is typically at least 15 amino acids or nucleotides in length, such as from about 15 to about 50, from about 20 to about 40 or from about 25 to about 30 amino acids or nucleotides in length.

In a preferred embodiment, the target analyte is a target polynucleotide and the section (i) is a polynucleotide which specifically hybridises to the target polynucleotide. The polynucleotide may be any of those discussed above. If the target polynucleotide is a miRNA, the sequence (i) is preferably RNA.

As discussed above, the duplex formed from the hybridisation of section (i) to the target polynucleotide temporarily holds a part of the probe, preferably a spacer (iv), in the narrowest part of the pore and this leads to change in current that can be measured. Typically, it temporarily leads to a steady measurable current flowing through the pore. A section (i) specifically hybridises to a target polynucleotide if it results in a measurable change in current, preferably a measureable change to a steady current, flowing through the pore in the presence of the target polynucleotide, but does not result in a measurable change in current, preferably a measureable change to a steady current, flowing though the pore in the absence of the target polynucleotide and presence of other polynucleotides. This can be measured as described in the Examples.

Preferably, the section (i) hybridises to the target polynucleotide with a melting temperature (Tm) that is at least 2° C., such as at least 3° C., at least 4° C., at least 5° C., at least 6° C., at least 7° C., at least 8° C., at least 9° C. or at least 10° C., greater than its Tm for the other members (i.e. the other target polynucleotides) in the group of two or more polynucleotides. More preferably, the section (i) hybridises to the target polynucleotide with a Tm that is at least 2° C., such as at least 3° C., at least 4° C., at least 5° C., at least 6° C., at least 7° C., at least 8° C., at least 9° C., at least 10° C., at least 20° C., at least 30° C. or at least 40° C., greater than its Tm for other polynucleotides. Preferably, the section (i) hybridises to the target polynucleotide with a Tm that is at least 2° C., such as at least 3° C., at least 4° C., at least 5° C., at least 6° C., at least 7° C., at least 8° C., at least 9° C., at least 10° C., at least 20° C., at least 30° C. or at least 40° C., greater than its Tm for a polynucleotide which differs from the target polynucleotide by one or more nucleotides, such as by 1, 2, 3, 4 or 5 or more nucleotides. The section (i) typically hybridises to the target polynucleotide with a Tm of at least 90° C., such as at least 92° C. or at least 95° C. Tm can be measured experimentally using known techniques or can be calculated using publicly-available Tm calculators, such as those available over the internet.

More preferably, the section (i) does not hybridise to the other members (i.e. the other target polynucleotides) in the group of two or more polynucleotides even under high stringency conditions. Most preferably, the section (i) does not hybridise to any other polynucleotide even under high stringency conditions. Such conditions are discussed in more detail below.

The section (i) is preferably a polynucleotide having at least 90% homologous based on nucleotide identity to the complement of the target polynucleotide over its entire length. The section (i) is more preferably a polynucleotide having at least 91%, at least 92%, at least 93%, at least 94%, at least 95%, at least 96%, at least 97%, at least 98% or at least 99% homologous based on nucleotide identity to the complement of the target polynucleotide over its entire length. Homology can be determined as discussed above. The section (i) is most preferably a polynucleotide which is complementary to the target polynucleotide over its entire length (i.e. identical to the complement of the target polynucleotide or member).

The probe(s) are preferably contacted with the sample under conditions which permit the section(s) (i) to hybridise to the target polynucleotide(s). Conditions that permit the hybridisation are well-known in the art (for example, Sambrook et al., 2001, Molecular Cloning: a laboratory manual, 3rd edition, Cold Spring Harbour Laboratory Press; and Current Protocols in Molecular Biology, Chapter 2, Ausubel et al., Eds., Greene Publishing and Wiley-Interscience, New York (1995)). Hybridisation can be carried out under low stringency conditions, for example in the presence of a buffered solution of 30 to 35% formamide, 1 M NaCl and 1% SDS (sodium dodecyl sulfate) at 37° C. followed by a wash in from 1× (0.1650 M Na+) to 2× (0.33 M Na+) SSC (standard sodium citrate) at 50° C. Hybridisation can be carried out under moderate stringency conditions, for example in the presence of a buffer solution of 40 to 45% formamide, 1 M NaCl, and 1% SDS at 37° C., followed by a wash in from 0.5× (0.0825 M Na+) to 1× (0.1650 M Na+) SSC at 55° C. Hybridisation can be carried out under high stringency conditions, for example in the presence of a buffered solution of 50% formamide, 1 M NaCl, 1% SDS at 37° C., followed by a wash in 0.1× (0.0165 M Na+) SSC at 60° C.

Preferred conditions are those described in the Example. In particular, the conditions are preferably 40 mM KCl, 10 mM HEPES, pH 8, and at 97° C. for 2.5 minutes. The temperature is then decreased by 0.1° C. every 5 seconds until the temperature reaches 20° C.

Sequence (ii)

The sequence (ii) is capable of forming a quadruplex. A quadruplex is a three dimensional structure formed from four sequence strands.

The quadruplex is not capable of translocating or moving through the narrowest part of the pore. The quadruplex is wider than the narrowest part of the pore. The narrowest part of wild-type α-HL pore is 1.3 nm is diameter. The narrowest part of α-HL-NN pore (one subunit of which shown in SEQ ID NO: 2) is 1.5 nm in diameter. If either of these pores are used in the invention, the quadruplex preferably has a width of greater than 1.3 nm, such as greater than 1.5 nm, such as greater than 2 nm, greater than 3 nm or greater than 5 nm. A person skilled in the art will be able to design a suitably sized quadruplex for the pore being used in the method. The sequence (ii) is capable of translocating or moving through the narrowest part of the pore when it is not formed into a quadruplex.

The sequence (ii) is preferably a polynucleotide. It may be any of the polynucleotides discussed above. The polynucleotide can be a nucleic acid, such as deoxyribonucleic acid (DNA) or ribonucleic acid (RNA). The polynucleotide in the sequence (ii) may be any synthetic nucleic acid known in the art, such as peptide nucleic acid (PNA), glycerol nucleic acid (GNA), threose nucleic acid (TNA), locked nucleic acid (LNA), morpholino nucleic acid or other synthetic polymers with nucleotide side chains.

The quadruplex may be any type of quadruplex. The quadruplex may be an intermolecular quadruplex, such as a bimolecular quadruplex or a tetramolecular quadruplex. The sequence (ii) is preferably capable of forming an intramolecular quadruplex.

The sequence (ii) is preferably capable of forming G-quadruplexes (also known as G-tetrads or G4-DNA). These are polynucleotide sequences that are rich in guanine and are capable of forming a four-stranded structure. Four guanine bases can associate through Hoogsteen hydrogen bonding to form a square planar structure called a guanine tetrad, and two or more guanine tetrads can stack on top of each other to form a G-quadruplex. The quadruplex structure is further stabilized by the presence of a cation, especially potassium, which sits in a central channel between each pair of tetrads. Forming G-quadruplexes is well known in the art (Marathias and Bolton, *Nucleic Acids Research*, 2000; 28(9): 1969-1977; Kankia and Marky, *J. Am. Chem. Soc.* 2001, 123, 10799-10804; and Marusic et al., *Nucleic Acids Research*, 2012, 1-11).

The sequence (ii) more preferably comprises the sequence Ga followed by Nb followed by Gc followed by Nd followed by Ge followed by Nf followed by Gg, wherein G is a nucleotide comprising guanine, wherein a, c, e and g are independently selected from 1, 2, 3, 4 and 5, wherein N is any nucleotide and wherein b, d and f are from 2 to 50. The values of a, c, e and g may be identical. G is preferably guanosine monophosphate (GMP), cyclic guanosine monophosphate (cGMP), deoxyguanosine monophosphate (dGMP), dideoxyguanosine monophosphate, N2-methyl-GMP, N2-methyl-cGMP, N2-methyl-dGMP, N2-methyl-dideoxyguanosine monophosphate, N2-methyl-O6-methyl-GMP, N2-methyl-O6-methyl-cGMP, N2-methyl-O6-methyl-dGMP, N2-methyl-O6-methyl-dideoxyguanosine monophosphate, 2'-O-methyl-GMP, 2'-O-methyl-cGMP, 2'-O-methyl-dGMP, 2'-O-methyl-dideoxyguanosine monophosphate, 6-thio-GMP, 6-thio-cGMP, 6-thio-dGMP, 6-thio-dideoxyguanosine monophosphate, 7-methyl-GMP, 7-methyl-cGMP, 7-methyl-dGMP, 7-methyl-dideoxyguanosine monophosphate, 7-deaza-GMP, 7-deaza-cGMP, 7-deaza-dGMP, 7-deaza-dideoxyguanosine monophosphate, 8-oxo-GMP, 8-oxo-cGMP, 8-oxo-dGMP or 8-oxo-dideoxyguanosine monophosphate.

Sequence (ii) preferably comprises the sequence shown in nucleotides 28 to 42 of SEQ ID NO: 11.

Since the quadruplex is incapable of translocating through the narrowest part of the pore, it acts like a brake and holds region (iii) in the narrowest part of the pore. Region (iii) then results in a distinctive current which identifies the probe, repeating unit or pair as discussed above. After a short while, the quadruplex will typically destabilise under the influence of the applied potential and unfold. The braking action of the quadruplex is therefore typically temporary. Region (iii) is typically only held in the narrowest part of the pore temporarily. The unfolded sequence (ii) translocates or moves through the pore under the influence of the applied potential.

Region (iii)

Each probe, repeating unit or pair (i.e. each type of probe, repeating unit or pair) in the panel comprises a region (iii) which is capable of entering the narrowest part of the pore when the quadruplex formed by the sequence (ii) cannot. The region (iii) is typically a linear molecule that is capable of entering and passing through the narrowest part of pore. Suitable molecules for forming the region (iii) are discussed below. When the region (iii) enters the narrowest part of the pore, it affects the current flowing through the pore in a distinctive manner. This manner is used to identify the probe, repeating unit or pair (and by association the target analyte). The distinctive current is typically caused by the specific structure of the region (iii) that is held in the narrowest part of the pore by the braking action of the quadruplex. This is discussed in more detail below.

The region (iii) preferably comprises a polymer. The polymer is capable of entering the pore and affecting the current flowing through the pore. The polymer is preferably a polynucleotide, a polypeptide or a polyethylene glycol (PEG).

When the polymer is a polynucleotide, it may comprise any of the nucleotides discussed above. However, the polynucleotide in the region (iii) typically comprises nucleotides selected from adenosine monophosphate (AMP), guanosine monophosphate (GMP), thymidine monophosphate (TMP), uridine monophosphate (UMP), cytidine monophosphate (CMP), cyclic adenosine monophosphate (cAMP), cyclic guanosine monophosphate (cGMP), deoxyadenosine monophosphate (dAMP), deoxyguanosine monophosphate (dGMP), deoxythymidine monophosphate (dTMP), deoxyuridine monophosphate (dUMP), deoxycytidine monophosphate (dCMP) and any of the modified nucleotides discussed above. The polynucleotide preferably comprises nucleotides selected from AMP, TMP, GMP, CMP, UMP, dAMP, dTMP, dGMP or dCMP. The polynucleotide preferably comprises one or more abasic nucleotides. The polynucleotide in the region (iii) may be single stranded or double stranded. The polynucleotide can be a nucleic acid, such as deoxyribonucleic acid (DNA) or ribonucleic acid (RNA). The polynucleotide in the region (iii) can comprise one strand of RNA hybridized to one strand of DNA. The polynucleotide in the region (iii) may be any synthetic nucleic acid known in the art, such as peptide nucleic acid (PNA), glycerol nucleic acid (GNA), threose nucleic acid (TNA), locked nucleic acid (LNA), morpholino nucleic acid or other synthetic polymers with nucleotide side chains.

Typically the region (iii) has a nucleic acid leader sequence, such as an abasic leader sequence, which leader sequence is the first region of the region (iii) to pass into the pore. When the region (iii) comprises a polynucleotide, preferably the region (iii) comprises at least 2 adjacent abasic residues, for example 3, 4, 5, 6, 7 or more adjacent abasic residues.

Although double stranded polynucleotides in the region (iii) typically cannot pass through the pore, they can be useful in the method of the invention. For instance, the region (iii) may comprise one or more double stranded polynucleotides or polynucleotide regions. The presence of such a double stranded region does not prevent the probe from moving through the pore, but instead simply delays the movement of the probe through the pore as one of the strands in the region is stripped from the probe under the influence of the potential. Such a delay can be seen as the current flowing through the pore is measured. Hence, including one or more double stranded polynucleotide regions in each region (iii) increases the number of possible signals that can be obtained from a population of regions (iii) and hence increases the number of analyte members that can be assayed using the method of the invention.

Different specific regions (iii) between probes, repeating units or pairs (i.e. between different types of probes, repeating units or pairs) have different effects on the current flowing through the pore and so can be distinguished from one another.

The region (iii) preferably comprises at least one single stranded polynucleotide or polynucleotide region. Single stranded polynucleotides are useful in the region (iii) because they can pass through the pore and can easily be designed to affect the current flowing through the pore in different ways. For instance, different polynucleotides having different sequences typically affect the current flowing through the pore in different ways. The region (iii) preferably comprises a polynucleotide barcode. Polynucleotide barcodes are well-known in the art (Kozarewa, I. et al., (2011), *Methods Mol. Biol.* 733, p 279-298). A barcode is a specific sequence of polynucleotide that affects the current flowing through the pore in a specific and known manner.

The polypeptide in the region (iii) may comprise any amino acids, including any of those discussed above. Different amino acid sequences will affect the current flowing through the pore in different ways and so specific regions (iii) may be designed as discussed above for polynucleotides. Any of the embodiments discussed above for polynucleotides apply to polypeptides (with the substitution of nucleotides with amino acids).

The region (iii) may comprise PEG. PEG will affect the current flowing through the pore in a specific manner.

The region (iii) may be any length. The region (iii) preferably comprises a polynucleotide from about 7 to about 200 nucleotides in length, such as from about 10 to about 150, from about 20 to about 100 or from about 30 to about 70 nucleotides in length.

The region (iii) may comprise any of the polynucleotides used in the Examples. In particular, the region (iii) preferably comprises nucleotides 1 to 26 of SEQ ID NO: 8 or nucleotides 1 to 27 of SEQ ID NO: 11.

Each region (iii) in each probe, repeating unit or pair (i.e. each type of region (iii) in each type of probe, repeating unit or pair) affects the current flowing through the pore in a distinctive manner. In other words, a region (iii) affects the current flowing through the pore in a manner that can be distinguished or differentiated from the way in which a different region (iii) affects the current flowing through the pore. This allows the identity of each region (iii) (i.e. each type of region (iii)) to be measured in accordance with the invention. It also allows the identity of each probe, repeating unit or pair (i.e. each type of probe, repeating unit or pair) to be measured in accordance with the invention. The binding of the probe to an analyte member can then be measured as discussed above. Since the identity of each probe, repeating unit or pair and the binding of each probe to an analyte member can be measured, the presence or absence of each analyte member can be determined.

The distinctive manner may concern the extent to which the current flowing through the pore is affected, i.e. a change in amount of current that flows through the pore as region (iii) is temporarily held in the narrowest part of the pore, and/or the time for which the current is affected by region (iii) (the "dwell time"). The distinctive manner may be the current level while the current is affected by region (iii). The information derived from the current disruptions is typically of greater value than the dwell time as the former provides more distinct signatures, whereas dwell times have broader distribution. The distinctive manner may concern the extent to which the variance of the current flowing the through the pore is affected. The variance may increase or decrease as a result of the region (iii). Control experiments may be carried out to ensure that different probes, repeating units, pairs or regions (iii) have different effects on the current flowing through the pore. Results from carrying out the method of the invention on a test sample can then be compared with those derived from such control experiments in order to determine whether a particular analyte is present or absent in the test sample.

The distinctiveness between probes, repeating units or pairs can be achieved via differences in the sequence (ii) paired with a region (iii). For instance, different quadruplexes have different stabilities. A more stable quadruplex will hold its paired region (iii) in the narrowest part of the pore for longer and this can be identified by measuring the current flowing through the pore. The opposite is also true, i.e. a less stable quadruplex will hold its paired region (iii) for less time and this can be identified by measuring the current flowing through the pore.

In preferred embodiments discussed above, the distinctiveness of a region (iii) is due to the specific structure capable of entering the narrowest part of the pore when the quadruplex cannot. Differences in structure between different regions (iii) can be designed based on the presence of different polymers or the presence of different sequences of the same type of polymer. It is straightforward to design a panel of probes that have the required distinctiveness.

Spacer

The probe preferably further comprises a spacer (iv) which affects the current flowing through the pore in a different manner from the region (iii). The spacer is positioned in the probe such that it is held in the narrowest part of the pore when the complex between section (i) and the target analyte prevents the probe from translocating or moving through the pore. If the region (iii) is located between the section (i) and the sequence (ii), i.e. (i)-(iii)-(ii), the spacer (iv) is preferably located on the other side of the section (i) from the region (iii), i.e. (iv)-(i)-(iii)-(ii). If the sequence (ii) is located between the sequence (i) and the region (iii), the spacer (iv) is preferably located between the section (i) and the sequence (ii), i.e. (i)-(iv)-(ii)-(iii). A person skilled in the art the capable of designing suitable probes comprising a spacer (iv).

The fact that the spacer (iv) and region (iii) affect the current flowing through the pore in different ways ensures that both binding of section (i) to the target analyte and the identity of the probe, repeating unit or pair can be clearly measured. The spacer (iv) preferably affects the current flowing through the pore in a distinctive manner. In other words, the spacer (iv) preferably affects the current flowing through the pore in a manner that can be distinguished or differentiated from the way in which a different spacer or a region (iii) affects the current flowing through the pore. Typically the current level will be the distinctive feature. This also allows a probe or repeating unit comprising the spacer (iv) to be identified in accordance with the invention. Methods for designing spacers (iv) which affect the current flowing through the pore in a distinctive manner are discussed above with reference to region (iii).

Apparatus and Conditions

Electrical measurements may be made using standard single channel recording equipment as describe in Stoddart, D. S., et al., (2009), *Proceedings of the National Academy of Sciences of the United States of America* 106, p 7702-'7'70'7, Lieberman K R et al, J Am Chem Soc. 2010; 132(50):17961-72, and International Application WO-2000/28312. Alternatively, electrical measurements may be made using a multi-channel system, for example as described in International Application WO-2009/077734 and International Application WO-2011/067559.

The methods may be carried out using any apparatus that is suitable for investigating a membrane/pore system in which a pore is inserted into a membrane. The method may be carried out using any apparatus that is suitable for transmembrane pore sensing. For example, the apparatus comprises a chamber comprising an aqueous solution and a barrier that separates the chamber into two sections. The barrier has an aperture in which the membrane containing the pore is formed.

The methods may be carried out using the apparatus described in International Application No. PCT/GB08/000562 (WO 2008/102120).

The methods involve measuring the current flowing through the pore. Therefore the apparatus may also comprise an electrical circuit capable of applying a potential and measuring an electrical signal across the membrane and pore. The methods may be carried out using a patch clamp or a voltage clamp. The methods preferably involve the use of a voltage clamp.

The methods may be carried out on a silicon-based array of wells where each array comprises 128, 256, 512, 1024 or more wells.

The methods of the invention may involve the measuring of a current flowing through the pore. Suitable conditions for measuring ionic currents through transmembrane pores are known in the art and disclosed in the Examples. The method is typically carried out with a voltage applied across the membrane and pore. The voltage used is typically from +2 V to −2 V, typically −400 mV to +400 mV. The voltage used is preferably in a range having a lower limit selected from −400 mV, −300 mV, −200 mV, −150 mV, −100 mV, −50 mV, −20 mV and 0 mV and an upper limit independently selected from +10 mV, +20 mV, +50 mV, +100 mV, +150 mV, +200 mV, +300 mV and +400 mV. The voltage used is more preferably in the range 100 mV to 240 mV and most preferably in the range of 120 mV to 220 mV. It is possible to increase discrimination between different nucleotides by a pore by using an increased applied potential.

The methods are typically carried out in the presence of any charge carriers, such as metal salts, for example alkali metal salt, halide salts, for example chloride salts, such as alkali metal chloride salt. Charge carriers may include ionic liquids or organic salts, for example tetramethyl ammonium chloride, trimethylphenyl ammonium chloride, phenyltrimethyl ammonium chloride, or 1-ethyl-3-methyl imidazolium chloride. In the exemplary apparatus discussed above, the salt is present in the aqueous solution in the chamber. Potassium chloride (KCl), sodium chloride (NaCl) or caesium chloride (CsCl) is typically used. KCl is preferred. The salt concentration may be at saturation. The salt concentration may be 3M or lower and is typically from 0.1 to 2.5 M, from 0.3 to 1.9 M, from 0.5 to 1.8 M, from 0.7 to 1.7 M, from 0.9 to 1.6 M or from 1 M to 1.4 M. The salt concentration is preferably from 150 mM to 1 M. The method is preferably carried out using a salt concentration of at least 0.3 M, such as at least 0.4 M, at least 0.5 M, at least 0.6 M, at least 0.8 M, at least 1.0 M, at least 1.5 M, at least 2.0 M, at least 2.5 M or at least 3.0 M. High salt concentrations provide a high signal to noise ratio and allow for currents indicative of binding/no binding to be identified against the background of normal current fluctuations.

The methods are typically carried out in the presence of a buffer. In the exemplary apparatus discussed above, the buffer is present in the aqueous solution in the chamber. Any buffer may be used in the method of the invention. Typically, the buffer is HEPES. Another suitable buffer is Tris-HCl buffer. The methods are typically carried out at a pH of from 4.0 to 12.0, from 4.5 to 10.0, from 5.0 to 9.0, from 5.5 to 8.8, from 6.0 to 8.7 or from 7.0 to 8.8 or 7.5 to 8.5. The pH used is preferably about 7.5.

The methods may be carried out at from 0° C. to 100° C., from 15° C. to 95° C., from 16° C. to 90° C., from 17° C. to 85° C., from 18° C. to 80° C., 19° C. to 70° C., or from 20° C. to 60° C. The methods are typically carried out at room temperature. The methods are optionally carried out at a temperature that supports enzyme function, such as about 37° C.

The sample and probe or panel of two or more probes may be contacted with the pore on either side of the membrane. The sample and probe or panel of two or more probes are typically contacted with the pore on the same side of the membrane.

The sample and the panel of probes may be contacted the pore in any order. It is preferred that the sample is contacted with the pore before the probe or panel or at the same time as the probe or panel. If the probe or panel is contacted with the pore before the sample is contacted with the pore, it is essential to ensure that sufficient probes remain available for binding to the analyte members (and have not all crossed the membrane through the pore). It is most preferred to contact the sample with the probe or panel and then contact the two with the pore.

Methods of Measuring Concentration

The method of the invention preferably further comprises, for those probes that bind an analyte member, comparing the different currents flowing through the pore when each probe is bound and unbound. This helps to determine the concentration of the analyte(s) present in the sample, generally by reference to a calibration curve, use of equilibrium constants or reference to control data. Methods for calculating the concentration are well known in the art.

The invention also provides a method of determining in a sample the concentration of a target analyte, the method comprising:

(i) carrying out the uniplex method of the invention; and (ii) if the target analyte is shown to be present in the sample comparing the current flowing through the pore in step (b) with control or reference data for the target analyte and thereby determining the concentration of the target analyte in the sample.

The invention also provides a method of determining in a sample the concentration of one or more members of a group of two or more target analytes, the method comprising:

(i) carrying out a multiplex method of the invention; and (ii) for one or more members shown to be present in the sample comparing the current flowing through the pore in step (b) with control or reference data for each member and thereby determining the concentration of the one or more members in the sample.

Control or reference data can be generated by conducting control experiments in which known concentrations of an analyte member are used to calibrate the assay.

Panels and Kits

The invention also provides a probe for determining the presence, absence or concentration of a target analyte. This is a uniplex probe. The probe comprises (i) a section which specifically binds to the target analyte, (ii) at least one sequence which is capable of forming a quadruplex, and (iii) at least one region which is specific for the section (i).

The invention also provides a probe for determining the presence, absence or concentration of one or more members of a group of two or more target analytes. This is a multiplex probe. The probe comprises two or more repeating units, wherein each repeating unit comprises (i) a section which specifically binds to one of the members, (ii) at least one sequence which is capable of forming a quadruplex, and (iii) at least one region which is specific for the section (i), and wherein each member is specifically recognised by at least one repeating unit.

The invention also provides a panel of probes for determining in a sample the presence, absence or concentration of one or more members of a group of two or more target analytes. The the panel comprises two or more probes, wherein each probe comprises one or more repeating units, wherein each repeating unit specifically recognises one of the members, wherein each repeating unit comprises (i) a section which specifically binds to the member, (ii) at least one sequence which is capable of forming a quadruplex, and (iii) at least one region which is specific for the section (i), and wherein each member of the group is specifically recognised by at least one repeating unit in the two or more probes.

The region (iii) is specific for the section (i) in the sense that it allows the section and hence the probe or repeating unit to be identified. This typically means that the region (iii) is capable of entering the narrowest part of a transmembrane pore when the quadruplex formed by the sequence (ii) cannot and affects the current flowing through the pore in a distinctive manner Any of the embodiments discussed above with reference to the method of the invention equally apply to the probe or panel of the invention.

The invention also provides a kit for determining in a sample the presence, absence or concentration of a target analyte or one or more members of a group of two or more target analytes. The kit comprises (a) a probe of the invention or a panel of probes of the invention and (b) a transmembrane pore. Any of the embodiments discussed above with reference to the method of the invention equally apply to the kits.

The kit may further comprise the components of a membrane, such as the phospholipids needed to form an amphiphilic layer, such as a lipid bilayer.

The kits of the invention may additionally comprise one or more other reagents or instruments which enable any of the embodiments mentioned above to be carried out. Such reagents or instruments include one or more of the following: suitable buffer(s) (aqueous solutions), means to obtain a sample from a subject (such as a vessel or an instrument comprising a needle), means to amplify and/or express polynucleotides, a membrane as defined above or voltage or patch clamp apparatus. Reagents may be present in the kit in a dry state such that a fluid sample resuspends the reagents. The kit may also, optionally, comprise instructions to enable the kit to be used in the method of the invention or details regarding which patients the method may be used for. The kit may, optionally, comprise nucleotides.

Apparatus

The invention also provides an analysis apparatus for determining in a sample the presence, absence or concentration of a target analyte or one or more members of a group of two or more target analytes. The apparatus comprises (a) a plurality of transmembrane pores and (b) a plurality of uniplex probes of the invention, a multiplex probe of the invention or a panel of probes of the invention. The apparatus preferably further comprises instructions for carrying out the method of the invention. The apparatus may be any conventional apparatus for polynucleotide analysis, such as an array or a chip. Any of the embodiments discussed above with reference to the methods of the invention are equally applicable to the apparatus of the invention.

The apparatus is preferably set up to carry out the method of the invention.

The apparatus preferably comprises:

a sensor device that is capable of supporting the plurality of pores and being operable to perform analyte analysis using the pores and probe(s) or panel; and at least one port for delivery of the material for performing the analysis.

The apparatus preferably comprises:

a sensor device that is capable of supporting the plurality of pores and being operable to perform analyte analysis using the pores and probe(s) or panel; and at least one reservoir for holding material for performing the analysis.

The apparatus more preferably comprises:

a sensor device that is capable of supporting the membrane and plurality of pores and being operable to perform analyte analysis using the pores;

at least one reservoir for holding material for performing the analysis;

a fluidics system configured to controllably supply material from the at least one reservoir to the sensor device; and one or more containers for receiving respective samples, the fluidics system being configured to supply the samples selectively from the containers to the sensor device. The apparatus may be any of those described in International Application No. PCT/GB08/004127 (published as WO 2009/077734), PCT/GB10/000789 (published as WO 2010/122293), International Application No. PCT/GB10/002206

(WO 2011/067559) or International Application No. PCT/US99/25679 (published as WO 00/28312).

The following Examples illustrate the invention.

Example 1

This example illustrates how by using a comparative probe (SEQ ID NO: 8, which has a cholesterol tether attached to its 3' end), which does not have a quadruplex, it was not possible to distinguish the presence or absence of the microRNA (SEQ ID NO: 7).

Materials and Methods 1.1—MicroRNA Hybridisation

MicroRNA sample (SEQ ID NO: 7, 10 µM) was heated to 97° C. with 10 µM of the comparative probe (SEQ ID NO: 8, which has a cholesterol tether attached to its 3' end), in a total volume of 50 µl, in 40 mM KCl, 10 mM HEPES, pH 8, for 2.5 minutes. The temperature was then decreased by 0.1° C. every 5 seconds until the temperature reached 20° C.

1.2—Nanopore Preparation

A solution of the αHL-(E111N/K147N)$_7$ (NN) (SEQ ID NO: 2) biological nanopore was prepared by in vitro transcription/translation (Stoddart, D. S., et al., (2009), *Proceedings of the National Academy of Sciences of the United States of America* 106, p 7702-'7'70'7) (1 µM diluted 1/80, 000) in 1 M KCl, 25 mM Tris, pH 7.5.

1.3—Experimental Setup

Single channel currents were recorded with an Axopatch 200A and 200B patch-clamp amplifier (Molecular Devices Inc., USA) with the cis compartment connected to ground, using lipid bilayers formed from 1,2-diphytanoyl-snglycero-3-phosphocholine (Avanti Polar Lipids). In both compartments of the recording chamber a buffer consisting of 1 ml 1 M KCl, 100 mM HEPES pH 8.0 was used. A suspension of NN α-hemolysin (SEQ ID NO: 2, 50 µM) was added to the cis compartment, the chamber was then perfused with 8 ml of fresh buffer as soon as a single pore had inserted into the bilayer.

A control programme, which cycled through periods of positive holding potential followed by rest periods where no potential was applied, was run for 5 minutes. The control programme applied a potential of 0 mV for 10 seconds, followed by a potential of +170 mV for a further 50 seconds and this cycle was repeated up to 20 times.

A potential of +180 mV was then applied to the trans side and recorded for a control period of 600 s, after which the probe (SEQ ID NO: 8, which has a cholesterol tether attached to its 3' end, 1 nM) was added to the cis chamber and data recorded for a further 1,200 s. Finally, the duplexes (SEQ ID NO: 7 hybridised to SEQ ID NO: 8, which has a cholesterol tether attached to its 3' end) were added to the cis compartment, recording for another 1,200 s. The translocation of a ssDNA strand by an α-HL pore is observed as a stepwise decrease in the open pore current level (IO) to a lower current level (IB). The amplified signal (arising from the ionic current passing through the pore) was low-pass filtered at 1 kHz and sampled at 20 kHz with a computer equipped with a Digidata 1440A digitizer (Molecular Devices).

1.4—Event Analysis

As the probes (SEQ ID NO: 8, which has a cholesterol tether attached to its 3' end) and probe: miRNA duplexes (SEQ ID NO: 7 hybridised to SEQ ID NO: 8, which has a cholesterol tether attached to its 3' end) interact with the nanopore, they produce characteristic current levels. The ratio of the number of duplex events to the number of probe-only events can be utilised to calculate the concentration of the target microRNA, by comparison to calibration curves generated from uniplexed microRNA titration experiments.

To identify changes in current level programmatically, a sliding window analysis is used, in which we passed two adjacent windows of length n through the current data, and at point i, we compared the intervals (i−n) to (i−1) and i to (i+n−1), using a t-statistic. If the data within the two windows are sufficiently different we conclude that they represent different states of the system, and that a transition between events occurred at point i.

Results

The probe used in this example was designed to have a leader at the 5' end, a region just beneath the section where the microRNA hybridises to the probe and a membrane tether at the 3' end (FIG. 1). By changing the sequence of the region in the probe, it was expected that different signals would result from different probes, in the presence of microRNA targets. However, the signals which corresponded to the probe (SEQ ID NO: 8, which has a cholesterol tether attached to its 3' end) in the absence of microRNA were too short (~0.004 s) for the sampling rate (20 kHz) of the experiment. This meant that it would be unlikely that reliable measurements of the block levels would be obtained and, therefore, it would not be possible to identify the probes from these levels. Therefore, this particular comparative probe design, which did not include a quadruplex, could not be used to distinguish between the presence and absence of microRNA targets.

Example 2

This example illustrates how by using a probe (SEQ ID NO: 9, which has a cholesterol tether attached to its 3' end), which was designed to have a leader at the 5' end, a region, a quadruplex located just beneath the section where the microRNA hybridises to the probe and a membrane tether at the 3' end, it was possible to distinguish the presence or absence of the microRNA (SEQ ID NO: 7).

Materials and Methods

The experimental procedure described in Example 1 was followed for Example 2 except the probe used was SEQ ID NO: 9 (shown below and which has a cholesterol tether attached to its 3' end).

Figure 2:
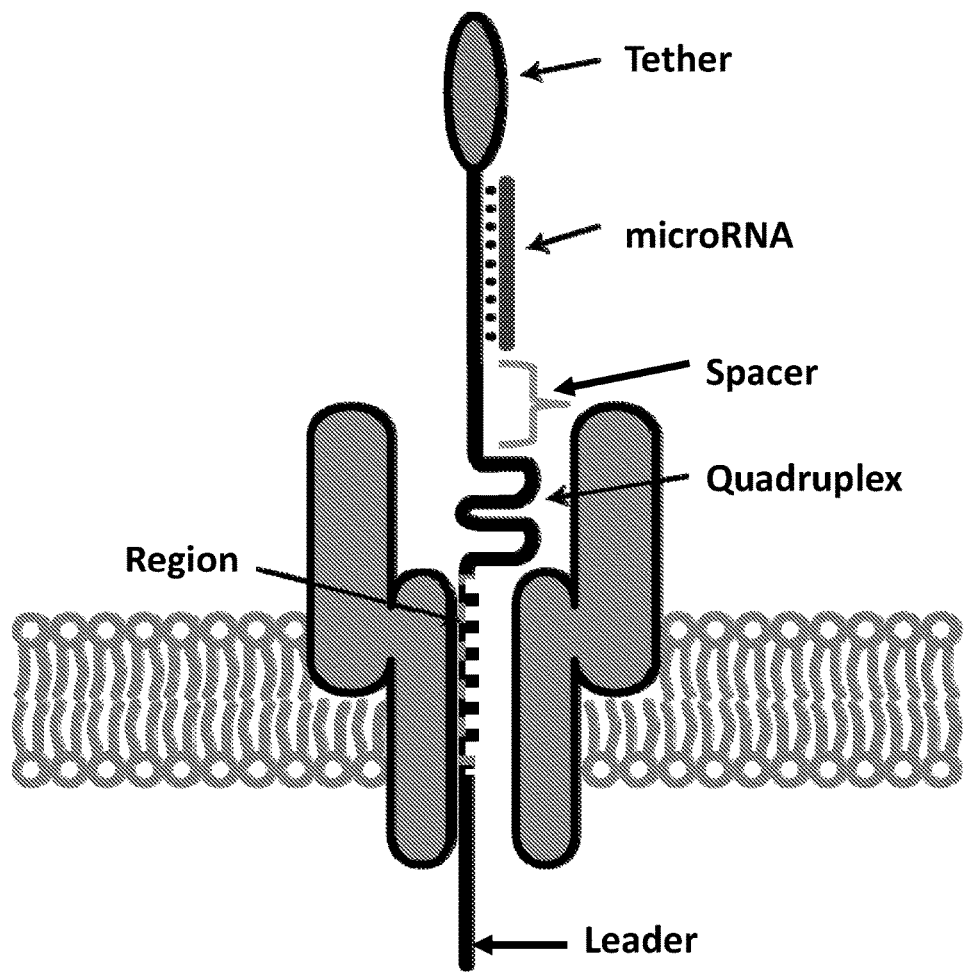
FIG. 2 shows the probe designed used in Examples 2 and 3.

(where X = an abasic)
SEQ ID NO: 9
TTTTTTTTTTTTTTTTTTTXXXXXXGGTTGGTGTGGTTGGTTTTTTTA
CCCCTATCACGATTAGCATTAATT Results The probe used in this example was similar in structure to the design used in Example 1 but the probe (SEQ ID NO: 9, which has a cholesterol tether attached to its 3' end) also contained a quadruplex in the middle (FIG. 2). Instead of having the region immediately beneath the section where the microRNA hybridises, the region was positioned immediately beneath the quadruplex. There was also a spacer, consisting of a fixed sequence (Ts in this case) between the microRNA hybridisation section and the quadruplex. It was anticipated that the translocation of the probe would be slowed by the quadruplex, regardless of whether or not the microRNA was hybridised. This would allow us to identify the probe. It was also anticipated that in the presence of the microRNA, a second signal would be obtained, as a result of the duplex blocking the pore, whereas in the absence of the microRNA, we would not see this signal. It might also be possible to see a signal caused by the duplex region denaturing or an interaction with the cholesterol.

Figure 3:
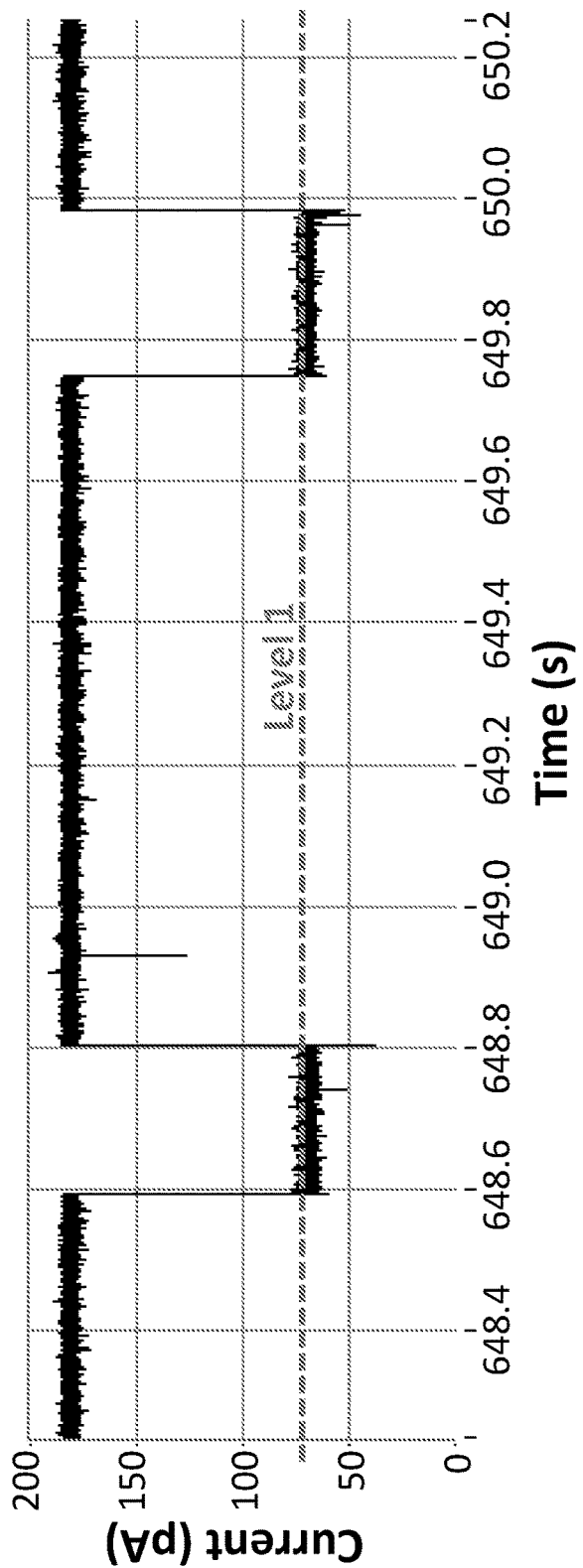
FIG. 3 shows the current block level (level 1) produced by the probe (SEQ ID NO: 9, which has a cholesterol tether at its 3' end) in the absence of microRNA (SEQ ID NO: 7).

In the absence of microRNA (SEQ ID NO: 7), translocation of the probe (SEQ ID NO: 9, which has a cholesterol tether attached to its 3' end) was interrupted by the presence of the quadruplex, giving a steady level which typically lasted for ~0.2 s (FIG. 3). This made the probe much easier to detect than it was in Example 1.

Figure 4:
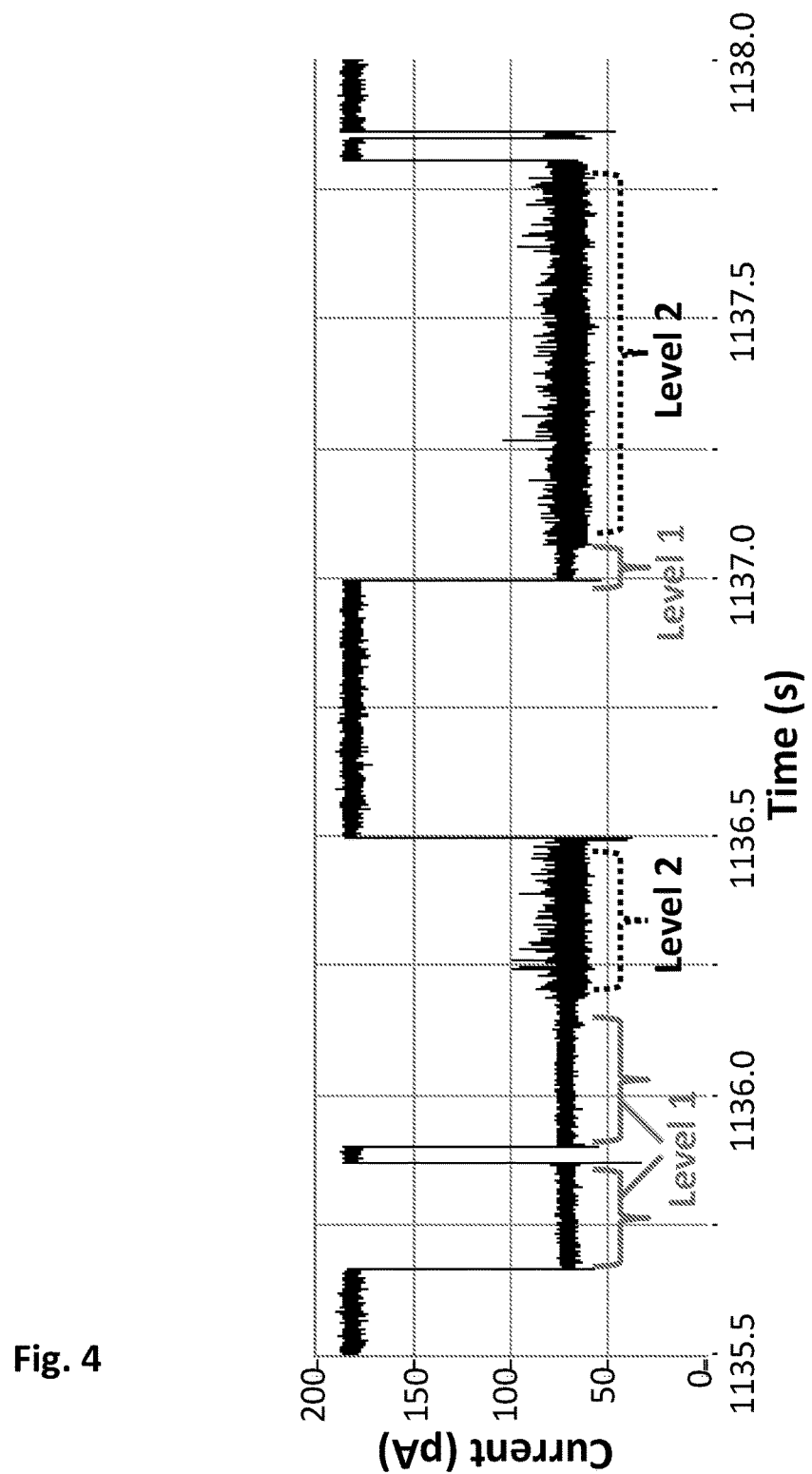
FIG. 4 shows the current block levels (level 1 and 2) produced by the probe (SEQ ID NO: 9, which has a cholesterol tether at its 3' end) in the presence of microRNA (SEQ ID NO: 7). Block level 1 is produced by the quadruplex inside the pore and block level 2 (which is much nosier than level 1) is produced by the miRNA/probe duplex.

In the presence of the microRNA (SEQ ID NO: 7), an additional level within the event was observed (FIG. 4, level 2). So the first part of the current block signal corresponds to the quadruplex (level 1), which is identical to the level seen in the absence of the microRNA target. Following this, a duplex level was observed which is much noisier than level 1. By adjusting the sequence of the region, we expect to be able to change the level of the first part of the block. The second part of the block may or may not differ for different microRNA hybridisation sections. It does not matter if level 2 is the same for different microRNAs since we identify the probe from the first level, and the presence of the second level corresponds to presence or absence of the microRNA.

Example 3

This example illustrates how by using the same probe design as was used in Example 2, it was possible to distinguish two different probes (SEQ ID NOs: 10 and 11, which both have a cholesterol tether at their 3' ends) which detect the presence or absence of the same microRNA (SEQ ID NO: 7).

Materials and Methods

The experimental procedure described in Example 1 was followed for Example 3 except the probes used were SEQ ID NOs: 10 (shown below) and 11 (which both have a cholesterol tether attached to their 3' ends).

Figure 5:
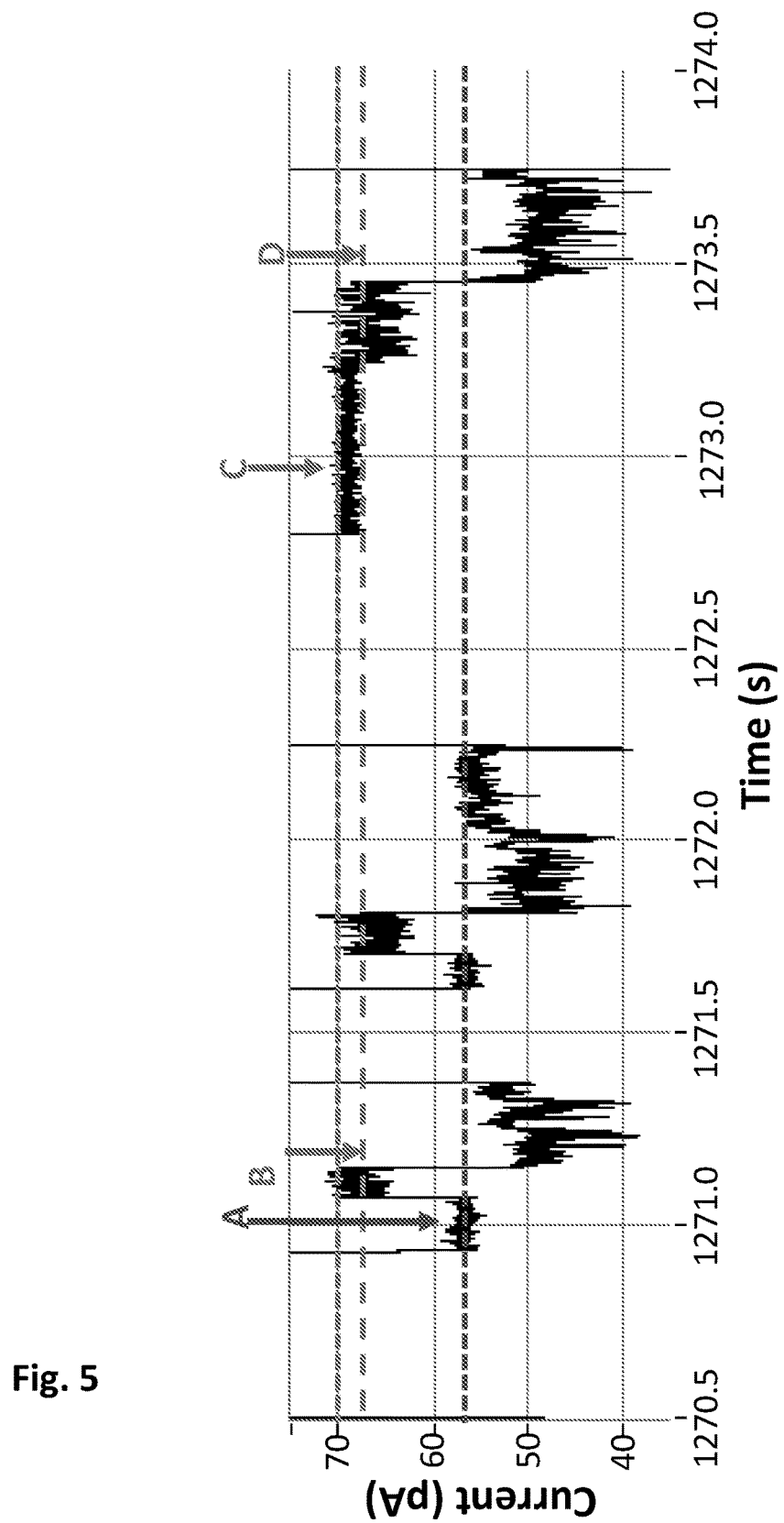
FIG. 5 shows the current block levels produced by the probes (SEQ ID NOs: 10 and 11, which both have a cholesterol tether at their 3' ends) in the presence of microRNA (SEQ ID NO: 7). There are three probe signals shown in the current trace, the first two correspond to the probe with SEQ ID NO: 11 and the third corresponds to the probe with SEQ ID NO: 10. Both probes have distinct first current block levels (labelled A for SEQ ID NO: 11 and labelled C for SEQ ID NO: 10) and the same second current block level (labelled B for SEQ ID NO: 11 and labelled D for SEQ ID NO: 10). This illustrates that it is possible to distinguish the same microRNA (SEQ ID NO: 7) using two different probes (SEQ ID NOs: 10 and 11, which both have a cholesterol tether at the 3' end) which differ only in their sequence of the region.

(where X =an abasic)
SEQ ID NO: 10
TTTTTTTTTTTTTTTTTTTTXXXXXXGGTTGGTGTGGTTGGTTTTTTTA CCCCTATCACGATTAGCATTAATT Results The probes used in this example were designed to confirm whether it was possible to distinguish two different probe signals for the same microRNA (SEQ ID NO: 7) which only differ in the sequence of the region which is below the quadruplex. It was anticipated that the first current block signal would be different for the two probes but the second current block level would be the same. FIG. 5 shows three probe signals, the first two correspond to the probe with SEQ ID NO: 11 and the third corresponds to the probe with SEQ ID NO: 10. Both probes have distinct first current block levels (labelled A for SEQ ID NO: 11 and labelled C for SEQ ID NO: 10) and the same second current block level for (labelled B for SEQ ID NO: 11 and labelled D for SEQ ID NO: 10). This illustrated that it was possible to distinguish the same microRNA (SEQ ID NO: 7) using two different probes (SEQ ID NOs: 10 and 11, which both have a cholesterol tether at the 3' end) which differ only in their sequence of the region. Due to the length of the α-HL barrel, it is straightforward to design further probes with elevated region block levels by including more abasic residues, and to design regions that have levels between the two shown in FIG. 5.

The invention claimed is:

1. A method of determining in a sample the presence or absence of a target analyte, the method comprising:
   (a) contacting the target analyte with a transmembrane pore and a probe,
   wherein the probe comprises (i) a section which is capable of translocating through the pore and which specifically binds to the target analyte, (ii) at least one sequence which is capable of forming a quadruplex, wherein the quadruplex is not capable of translocating through the narrowest part of the pore, and (iii) at least one region which is capable of entering the narrowest part of the pore when the quadruplex formed by sequence (ii) cannot and which affects the current flowing through the pore in a distinctive manner; and
   (b) measuring the current flowing through the pore to determine whether or not the probe has bound to the target analyte and thereby determining the presence or absence of the target analyte in the sample.

2. A method according to claim 1, wherein binding of the probe to the target analyte is determined by the presence of a current which is indicative of the probe being prevented from translocating through the pore by the complex formed by binding of the section (i) to the target analyte.

3. A method of determining in a sample the presence or absence of one or more members of a group of two or more target analytes, the method comprising:
   (a) contacting the sample with a transmembrane pore and one or more probes,
   wherein each probe comprises one or more repeating units,
   wherein each repeating unit specifically recognises one of the members,
   wherein each repeating unit comprises (i) a section which is capable of translocating through the pore and which specifically binds to the member, (ii) at least one sequence which is capable of forming a quadruplex, wherein the quadruplex is not capable of translocating through the narrowest part of the pore, and (iii) at least one region which is capable of entering the narrowest part of the pore when the quadruplex formed by sequence (ii) cannot and which affects the current flowing through the pore in a distinctive manner,
   and wherein each member of the group is specifically recognised by at least one repeating unit in the one or more probes; and
   (b) measuring the current flowing through the pore to determine which repeating units in the one or more probes, if any, have bound to a member and thereby determining the presence or absence of one or more members in the sample.

4. A method according to claim 3, wherein the sample is contacted with (a) one probe which comprises two or more repeating units, (b) a panel of two or more probes, wherein each probe comprises one or more of the repeating units, (c) a panel of two or more probes, wherein each probe comprises one or more of the repeating units or (d) a panel of two or more probes, wherein each probe comprises one or more of the repeating units and wherein the number of probes in the panel is identical to the number of members in the group of target analytes.

5. A method according to claim 3, wherein binding of a repeating unit to a member is determined by the presence of a current which is indicative of the repeating unit being prevented from translocating through the pore by the complex formed by binding of the section (i) to the member.

6. A method according to claim 3, wherein (a) the repeating unit is identified on the basis of the distinctive current provided by at least one region (iii) or each repeating unit comprises a different region (iii).

7. A method according to claim 1, wherein the at least one sequence (ii) capable of forming a quadruplex is located between the section (i) and the at least one region (iii).

8. A method according to claim 1, wherein the sequence (ii) is a polynucleotide, is capable of forming an intramolecular quadruplex or comprises the sequence shown in nucleotides 28 to 42 of SEQ ID NO: 11.

9. A method according to claim 1, wherein the region (iii) comprises (a) a polymer, (b) a polynucleotide, a polypeptide or a polyethylene glycol (PEG) or (c) a polynucleotide from about 7 to about 200 nucleotides in length.

10. A method according to claim 1, wherein the probe is coupled to the membrane or coupled to the membrane using cholesterol.

11. A method according to claim 1, wherein the target analyte is a single-stranded polynucleotide of from about 15 to about 30 nucleotides in length.

12. A method according to claim 11, wherein the sequence (i) specifically hybridises to the target polynucleotide or is at least 90% homologous based on nucleotide identity to the complement of the target polynucleotide over its entire length.

13. A method according to claim 11, wherein the target polynucleotide is a microRNA (miRNA) or a miRNA which can be used to diagnose or prognose a disease or condition.

14. A method according to claim 1, wherein the pore is (a) a transmembrane protein pore or a solid state pore; (b) a transmembrane protein pore derived from a hemolysin, leukocidin, *Mycobacterium smegmatis* porin A (MspA), lysenin, outer membrane phospholipase A, *Neisseria* autotransporter lipoprotein (NalP) and WZA; (c) formed of seven identical subunits as shown in SEQ ID NO: 2 or a variant thereof in which one or more of the seven subunits has at least 50% homology to SEQ ID NO: 2 based on amino acid identity over the entire sequence and which retains pore activity or (d) γ-hemolysin formed of four identical subunits as shown in SEQ ID NO: 4 and four identical subunits as shown in SEQ ID NO: 6 or a variant thereof in which one or more of the subunits has at least 50% homology to SEQ ID NO: 4 based on amino acid identity over the entire sequence and/or one or more of the subunits has at least 50% homology to SEQ ID NO: 6 based on amino acid identity over the entire sequence and the pore retains pore activity.

15. A method of determining in a sample the concentration of a target analyte, the method comprising:
(i) carrying out a method according to claim 1; and
(ii) if the target analyte is shown to be present in the sample comparing the current flowing through the pore in step (b) with control or reference data for the target analyte and thereby determining the concentration of the target analyte in the sample.

16. A method of determining in a sample the concentration of one or more members of a group of two or more target analytes, the method comprising:
(i) carrying out a method according to claim 3; and
(ii) for one or more members shown to be present in the sample comparing the current flowing through the pore in step (b) with control or reference data for each member and thereby determining the concentration of the one or more members in the sample.

* * * * *

SEQUENCE LISTING

```
<160> NUMBER OF SEQ ID NOS: 11

<210> SEQ ID NO 1
<211> LENGTH: 885
<212> TYPE: DNA
<213> ORGANISM: Artificial Sequence
<220> FEATURE:
<223> OTHER INFORMATION: Synthetic polynucleotide

<400> SEQUENCE: 1
atggcagatt ctgatattaa tattaaaacc ggtactacag atattggaag caatactaca      60
gtaaaaacag gtgatttagt cacttatgat aaagaaaatg gcatgcacaa aaaagtattt     120
tatagtttta tcgatgataa aaatcacaat aaaaaactgc tagttattag aacaaaaggt     180
accattgctg gtcaatatag agtttatagc gaagaaggtg ctaacaaaag tggtttagcc     240
tggccttcag cctttaaggt acagttgcaa ctacctgata atgaagtagc tcaaatatct     300
gattactatc caagaaattc gattgataca aaaaactata tgagtacttt aacttatgga     360
ttcaacggta atgttactgg tgatgataca ggaaaaattg gcggccttat tggtgcaaat     420
gtttcgattg gtcatacact gaactatgtt caacctgatt tcaaaacaat tttagagagc     480
ccaactgata aaaagtagg ctggaaagtg atatttaaca atatggtgaa tcaaaattgg     540
ggaccatacg atcgagattc ttggaacccg gtatatggca atcaacttt catgaaaact      600 agaaatggtt ctatgaaagc agcagataac ttccttgatc ctaacaaagc aagttctcta     660
ttatcttcag ggttttcacc agacttcgct acagttatta ctatggatag aaaagcatcc     720
aaacaacaaa caaatataga tgtaatatac gaacgagttc gtgatgatta ccaattgcat     780
```
tggacttcaa caaattggaa aggtaccaat actaaagata aatggacaga tcgttcttca    840
gaaagatata aaatcgattg ggaaaaagaa gaaatgacaa attaa    885

<210> SEQ ID NO 2
<211> LENGTH: 293
<212> TYPE: PRT
<213> ORGANISM: Artificial Sequence
<220> FEATURE:
<223> OTHER INFORMATION: Synthetic polypeptide

<400> SEQUENCE: 2

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Asn Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Asn Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
    290

<210> SEQ ID NO 3
<211> LENGTH: 903
<212> TYPE: DNA
<213> ORGANISM: Staphylococcus aureus

<400> SEQUENCE: 3

```
atggcggaag gcaaaattac cccggttagc gtgaaaaaag ttgatgacaa agtgaccctg      60
tataaaacga cggcgacggc ggatagcgat aaatttaaaa ttagccagat cctgaccttc     120
aacttcatca agacaaatc ttatgataaa gacaccctgg ttctgaaagc gacgggcaac     180
atcaatagcg gttttgtcaa accgaacccg aatgattacg acttctcaaa actgtattgg     240
ggcgccaaat acaatgtctc gattagctct cagagtaacg attccgtgaa tgcggttgac     300
tatgccccga aaaccaaaa cgaagaattc caggttcaaa acaccctggg ttacacgttc     360
ggcggtgata tttcaatctc gaatggcctg agtggcggtc tgaacggtaa taccgcattt     420
tccgaaacga ttaactataa acaggaaagc taccgtaccc tgtctcgcaa cacgaattat     480
aaaaacgtcg gctggggtgt ggaagcgcat aaaatcatga atggctgggg tccgtatggc     540
cgtgattcct ttcaccccgac ctacggcaac gaactgttcc tggcaggtcg ccagagttcc     600
gcgtatgccg gtcaaaattt tattgctcag catcaaatgc cgctgctgag ccgttctaac     660
tttaatccgg aattcctgtc agtgctgtcg caccgtcagg atcgcgcgaa aaaatctaaa     720
atcaccgtta cgtaccagcg tgaaatggac ctgtaccaaa tccgctggaa tggcttctat     780
tgggcaggtg ctaactacaa aaattttaaa acccgcacgt tcaaatctac ctatgaaatc     840
gattgggaaa atcacaaagt caaactgctg gacaccaaag aaaccgaaaa caacaaataa     900
taa                                                                   903

<210> SEQ ID NO 4
<211> LENGTH: 298
<212> TYPE: PRT
<213> ORGANISM: Staphylococcus aureus

<400> SEQUENCE: 4

Ala Glu Gly Lys Ile Thr Pro Val Ser Val Lys Lys Val Asp Asp Lys
1               5                   10                  15

Val Thr Leu Tyr Lys Thr Thr Ala Thr Ala Asp Ser Asp Lys Phe Lys
            20                  25                  30

Ile Ser Gln Ile Leu Thr Phe Asn Phe Ile Lys Asp Lys Ser Tyr Asp
        35                  40                  45

Lys Asp Thr Leu Val Leu Lys Ala Thr Gly Asn Ile Asn Ser Gly Phe
    50                  55                  60

Val Lys Pro Asn Pro Asn Asp Tyr Asp Phe Ser Lys Leu Tyr Trp Gly
65                  70                  75                  80

Ala Lys Tyr Asn Val Ser Ile Ser Ser Gln Ser Asn Asp Ser Val Asn
                85                  90                  95

Ala Val Asp Tyr Ala Pro Lys Asn Gln Asn Glu Glu Phe Gln Val Gln
            100                 105                 110

Asn Thr Leu Gly Tyr Thr Phe Gly Gly Asp Ile Ser Ile Ser Asn Gly
        115                 120                 125

Leu Ser Gly Gly Leu Asn Gly Asn Thr Ala Phe Ser Glu Thr Ile Asn
    130                 135                 140

Tyr Lys Gln Glu Ser Tyr Arg Thr Leu Ser Arg Asn Thr Asn Tyr Lys
145                 150                 155                 160

Asn Val Gly Trp Gly Val Glu Ala His Lys Ile Met Asn Gly Trp Gly
                165                 170                 175

Pro Tyr Gly Arg Asp Ser Phe His Pro Thr Tyr Gly Asn Glu Leu Phe
            180                 185                 190

Leu Ala Gly Arg Gln Ser Ser Ala Tyr Ala Gly Gln Asn Phe Ile Ala
        195                 200                 205
```

```
Gln His Gln Met Pro Leu Leu Ser Arg Ser Asn Phe Asn Pro Glu Phe
    210                 215                 220

Leu Ser Val Leu Ser His Arg Gln Asp Arg Ala Lys Lys Ser Lys Ile
225                 230                 235                 240

Thr Val Thr Tyr Gln Arg Glu Met Asp Leu Tyr Gln Ile Arg Trp Asn
                245                 250                 255

Gly Phe Tyr Trp Ala Gly Ala Asn Tyr Lys Asn Phe Lys Thr Arg Thr
                260                 265                 270

Phe Lys Ser Thr Tyr Glu Ile Asp Trp Glu Asn His Lys Val Lys Leu
            275                 280                 285

Leu Asp Thr Lys Glu Thr Glu Asn Asn Lys
        290                 295
```

```
<210> SEQ ID NO 5
<211> LENGTH: 849
<212> TYPE: DNA
<213> ORGANISM: Staphylococcus aureus

<400> SEQUENCE: 5
atggaaaaca aaatcgaaga catcggtcaa ggcgctgaaa tcatcaaacg cacgcaggac      60
attacctcta acgtctggc tattacccag aatattcaat tcgatttcgt gaaagacaaa     120
aaatacaaca agatgcact ggtggttaaa atgcagggct ttatcagctc tcgtaccacg     180
tacagcgatc tgaaaaaata tccgtacatt aaacgcatga tctggccgtt ccagtacaac     240
attagtctga aaccaaaga ttccaacgtg gacctgatta ttacctgcc gaaaaacaaa      300
atcgatagtg cggacgtttc ccagaaactg gctataaca ttggcggtaa ttttcaatca      360
gccccgtcga tcggcggtag tggttccttc aattactcaa aaaccatctc gtacaaccag    420
aaaaattacg ttacggaagt cgaaagccaa aactctaaag gcgtgaaatg gggtgttaaa    480
gcgaattcat ttgtcacccc gaacggccag gtgtcggcgt atgatcagta cctgtttgca    540
caagacccga cgggtccggc agcacgtgat tatttcgttc cggacaatca gctgccgccg    600
ctgattcaaa gcggctttaa cccgtctttc atcaccacgc tgtcccatga acgtggcaaa    660
ggtgataaaa gcgaatttga attaccctat ggtcgcaaca tggatgcaac ctatgcttac    720
gttacgcgtc atcgcctggc agtcgatcgt aaacacgacg ctttcaaaaa ccgcaatgtc    780
accgtgaaat acgaagtcaa ctggaaaacg cacgaagtca aatcaaaag tatcacgccg    840
aaataataa                                                            849
```

```
<210> SEQ ID NO 6
<211> LENGTH: 280
<212> TYPE: PRT
<213> ORGANISM: Staphylococcus aureus

<400> SEQUENCE: 6

Glu Asn Lys Ile Glu Asp Ile Gly Gln Gly Ala Glu Ile Ile Lys Arg
1               5                   10                  15

Thr Gln Asp Ile Thr Ser Lys Arg Leu Ala Ile Thr Gln Asn Ile Gln
            20                  25                  30

Phe Asp Phe Val Lys Asp Lys Lys Tyr Asn Lys Asp Ala Leu Val Val
        35                  40                  45

Lys Met Gln Gly Phe Ile Ser Ser Arg Thr Thr Tyr Ser Asp Leu Lys
    50                  55                  60

Lys Tyr Pro Tyr Ile Lys Arg Met Ile Trp Pro Phe Gln Tyr Asn Ile
65                  70                  75                  80
```

-continued

```
Ser Leu Lys Thr Lys Asp Ser Asn Val Asp Leu Ile Asn Tyr Leu Pro
            85                  90                  95

Lys Asn Lys Ile Asp Ser Ala Asp Val Ser Gln Lys Leu Gly Tyr Asn
            100                 105                 110

Ile Gly Gly Asn Phe Gln Ser Ala Pro Ser Ile Gly Gly Ser Gly Ser
            115                 120                 125

Phe Asn Tyr Ser Lys Thr Ile Ser Tyr Asn Gln Lys Asn Tyr Val Thr
            130                 135                 140

Glu Val Glu Ser Gln Asn Ser Lys Gly Val Lys Trp Gly Val Lys Ala
145                 150                 155                 160

Asn Ser Phe Val Thr Pro Asn Gly Gln Val Ser Ala Tyr Asp Gln Tyr
                165                 170                 175

Leu Phe Ala Gln Asp Pro Thr Gly Pro Ala Ala Arg Asp Tyr Phe Val
            180                 185                 190

Pro Asp Asn Gln Leu Pro Pro Leu Ile Gln Ser Gly Phe Asn Pro Ser
            195                 200                 205

Phe Ile Thr Thr Leu Ser His Glu Arg Gly Lys Gly Asp Lys Ser Glu
            210                 215                 220

Phe Glu Ile Thr Tyr Gly Arg Asn Met Asp Ala Thr Tyr Ala Tyr Val
225                 230                 235                 240

Thr Arg His Arg Leu Ala Val Asp Arg Lys His Asp Ala Phe Lys Asn
                245                 250                 255

Arg Asn Val Thr Val Lys Tyr Glu Val Asn Trp Lys Thr His Glu Val
            260                 265                 270

Lys Ile Lys Ser Ile Thr Pro Lys
            275                 280

<210> SEQ ID NO 7
<211> LENGTH: 23
<212> TYPE: RNA
<213> ORGANISM: Artificial Sequence
<220> FEATURE:
<223> OTHER INFORMATION: Synthetic polynucleotide

<400> SEQUENCE: 7
uuaaugcuaa ucgugauagg ggu                                          23

<210> SEQ ID NO 8
<211> LENGTH: 89
<212> TYPE: DNA
<213> ORGANISM: Artificial Sequence
<220> FEATURE:
<223> OTHER INFORMATION: Synthetic polynucleotide

<400> SEQUENCE: 8
tttttttttt cttttttttt tcttttttttt ttcttttttt tttctttttt ttttctttt   60 tttttacccc tatcacgatt agcattaat                                    89

<210> SEQ ID NO 9
<211> LENGTH: 74
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (21)..(26)
<223> OTHER INFORMATION: n is an abasic site

<400> SEQUENCE: 9
```

```
tttttttttt tttttttttt nnnnnnggtt ggtgtggttg gttttttttta ccCctatcac    60 gattagcatt aatt                                                       74

<210> SEQ ID NO 10
<211> LENGTH: 74
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (21)..(26)
<223> OTHER INFORMATION: n is an abasic site

<400> SEQUENCE: 10
tttttttttt tttttttttt nnnnnnggtt ggtgtggttg gttttttttta ccCctatcac    60 gattagcatt aatt                                                       74

<210> SEQ ID NO 11
<211> LENGTH: 75
<212> TYPE: DNA
<213> ORGANISM: Artificial Sequence
<220> FEATURE:
<223> OTHER INFORMATION: Synthetic polynucleotide

<400> SEQUENCE: 11
tttttttttt ctttttttttt cttttttggt tggtgtggtt ggttttttttt acccctatca   60 cgattagcat taatt                                                      75
```